(12) United States Patent
Beck et al.

(10) Patent No.: US 7,982,007 B2
(45) Date of Patent: Jul. 19, 2011

(54) CYNOMOLGUS TOLL-LIKE RECEPTOR 3

(75) Inventors: Heena Beck, Radnor, PA (US); Jill Carton, Radnor, PA (US)

(73) Assignee: Centocor, Inc., Malvern, PA (US)

( * ) Notice: Subject to any disclaimer, the term of this patent is extended or adjusted under 35 U.S.C. 154(b) by 329 days.

(21) Appl. No.: 12/342,332

(22) Filed: Dec. 23, 2008

(65) Prior Publication Data

US 2009/0176238 A1 Jul. 9, 2009

Related U.S. Application Data

(60) Provisional application No. 61/016,649, filed on Dec. 26, 2007.

(51) Int. Cl.
| | |
|---|---|
| C07K 14/47 | (2006.01) |
| C12N 15/64 | (2006.01) |
| C12N 15/24 | (2006.01) |
| C12P 21/02 | (2006.01) |

(52) U.S. Cl. ............... 530/351; 424/85.2; 435/69.52; 435/320.1; 435/471; 435/325; 536/23.5

(58) Field of Classification Search ................ None
See application file for complete search history.

(56) References Cited

U.S. PATENT DOCUMENTS

| | | |
|---|---|---|
| 2003/0166001 A1 | 9/2003 | Lipford |
| 2006/0115475 A1 | 6/2006 | Carton et al. |

OTHER PUBLICATIONS

Bell et al, PNAS, 2005, vol. 102, No. 31, pp. 10976-10980.*
Cho et al, Science, 2005, vol. 309, pp. 581-585.*
Alexopoulou, et al., "Recognition of double-stranded RNA and activation of NF-$_\kappa$B by Toll-like receptor 3," Nature, 413: 732-738 (2001).
Van Amersfoort, et al., Receptors, Mediators, and Mechanisms Involved in Bacterial Sepsis and Septic Shock, Clinical Microbiology Reviews, 16(3): 379-414 (2003).
Takeda, et al., "Microbial recognition by Toll-like receptors," Journal of Dermatological Science, 34: 73-82 (2004).
Pierre Miossec, "An update on the cytokine network in rheumatoid arthritis," Current Opinions in Rheumatology, 16: 218-222 (2004).
Ogata, et al., "Cytokine and Anti-cytokine Therapies for Inflammatory Bowel Disease," Current Pharmaceutical Design, 9: 1107-1113 (2003).
Sanghavi, et al., "Increased Expression of TLR3 in Lymph Nodes during Simian Immunodeficiency Virus Infection: Implications for Inflammation and Immunodeficiency," The Journal of Immunology, 175: 5314-5323 (2005).
PCT International Search Report dated May 7, 2009.

* cited by examiner

*Primary Examiner* — Bridget E Bunner
*Assistant Examiner* — Fozia Hamud
(74) *Attorney, Agent, or Firm* — Kirk Baumeister

(57) ABSTRACT

Isolated polynucleotides encoding Cynomolgus monkey Toll-Like Receptor 3 (cynoTLR3), polypeptides obtainable from expression of these polynucleotides, recombinant cells, methods and uses of these are disclosed.

4 Claims, 2 Drawing Sheets

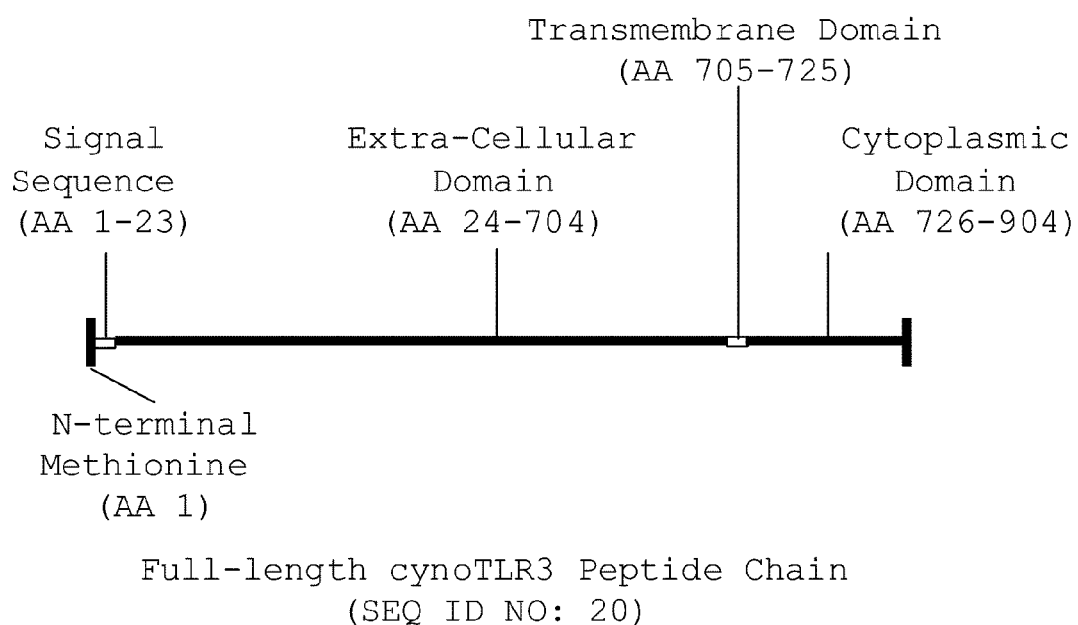

_US 7,982,007 B2_

CYNOMOLGUS TOLL-LIKE RECEPTOR 3

CROSS-REFERENCE TO RELATED APPLICATIONS

This application claims the benefit of U.S. Provisional Application Ser. No. 61/016,649, filed 26 Dec. 2007, the entire contents of which is incorporated herein by reference in its entirety.

FIELD OF THE INVENTION

The present invention relates to Cynomolgus monkey Toll-Like Receptor 3 (cynoTLR3) and its uses.

BACKGROUND OF THE INVENTION

Recognition of microbial antigens by the host immune system is mediated through innate immune receptors, whose activation represents an important step in the initiation of an inflammatory response. Toll-Like Receptors (TLR) are a family of innate immune receptors that play a crucial role in mediating an immune response to foreign antigens. TLR3s are pathogen associated molecular pattern recognition receptors that recognize double-stranded RNA (dsRNA) as well as the synthetic dsRNA analog poly-riboinosinic-ribocytidylic acid (poly(I:C)). See e.g. Alexopoulou et al., 413 *Nature* 732 (2001)). Moreover, TLR3 has been shown to recognize endogenous ligands such as mRNA released from necrotic cells suggesting that necrotic cell death at inflammation sites may contribute to activation of TLR3. See e.g. Kariko et al., 26 *J. Biol. Chem.* 12542 (2004).

Activation of TLR3s by dsRNA or poly(I:C) ligands induces secretion of pro-inflammatory cytokines and chemokines and can modulate disease outcomes during infection-associated inflammation. Importantly, TLR3 activation in vivo occurs in the context of viral infection or necrosis associated with inflammation. See Tabeta et al., 101 *Proc. Natl. Acad. Sci. USA* 3516 (2004)); see also Kariko et al., 26 *J. Biol. Chem.* 12542 (2004). For example, the human TLR3 peptide chain is expressed in the central nervous system (CNS), where it is required to control infection by the HSV-1 virus, which spreads from the epithelium to the central nervous system via cranial nerves to cause herpes simplex encephalitis in TLR3 deficient patients. See e.g. Zhang et al., 317 *Science* 1522 (2007). Furthermore, human TLR3 peptide chain activation results in inflammatory responses associated with pathological conditions such as, for example, primary biliary cirrhosis of liver tissues. See e.g. Takii et al., 85 *Lab. Invest.* 836 (2005).

Overall, these data demonstrate that activation of TLR3 initiates cascades of phosphorylation and transcriptional activation events that result in the production of numerous inflammatory cytokines that contribute to innate immunity (reviewed by Takeda and Akira, *J. Derm. Sci.* 34:73-82 (2004)). Further, these data indicate that sustained TLR3 activation is a critical component in the modulation of infection-associated inflammatory diseases. Published data lend further support to this hypothesis as shown by findings that associate over-production of pro-inflammatory cytokines to systemic inflammatory response syndrome, infection-associated acute cytokine storms (reviewed by Van Amersfoort et al., *Clin. Microbiol. Rev.* 16: 379-414 (2003)) and immune-mediated chronic conditions such as rheumatoid arthritis (reviewed by Miossec et al., *Curr. Opin. Rheumatol.* 16:218-222 (2004)) and inflammatory bowel diseases (reviewed by Ogata and Hibi, *Curr. Pharm. Des.* 9: 1107-1113 (2003)).

Currently, a number of different therapeutic approaches have been taken to target the activity of TLR3s for treatment of different indications. These TLR3 therapeutics include human peptide chain based TLR3 therapeutics, monoclonal antibody antagonists of TLR3, and TLR3 ligand agonists such as dsRNA, poly(I:C) as well as functional analogs of these that target TLR3 activity. The potential indications for monoclonal antibody antagonist based TLR3 therapeutics include inflammatory conditions, sepsis, inflammatory bowel disease, inflammatory pulmonary disease, and autoimmune diseases. The potential indications and uses for TLR3 therapeutics that are agonists include post-viral fatigue syndrome, glioma, prostate cancer, antiviral vaccines, bladder cancer, cervical dysplasia, human papilloma virus infection, breast cancer, viral infection prevention, tissue regeneration, and avian influenza vaccines.

Extensive safety testing will be required before any TLR3 therapeutic for human use can be brought to the market place. Such safety testing will involve both in vivo safety testing in animal models as well as the in vitro testing of TLR3 therapeutics. For example, antibody based TLR3 therapeutics may require the generation of surrogate antibodies against a TLR3 peptide chain expressed by a particular model animal as well as significant in vitro characterization of such surrogate antibodies. Such surrogate generation and in vitro characterization will require the use of TLR3 polynucleotides and peptide chains from a suitable model animal. Importantly, the identification of suitable animal models for such safety testing requires the identification of animal species capable of expressing a TLR3 with high identity and homology to human TLR3 (SEQ ID NO: 13).

Thus, a need exists for the identification of polynucleotides encoding TLR3s and TLR3 peptide chains capable of being expressed in an animal model suitable for the safety testing of TLR3 therapeutics. A need also exists for related methods such as methods of expressing peptide chains and testing the safety of a TLR3 therapeutic in an animal model identified as suitable for safety assessment of TLR3 therapeutics.

BRIEF DESCRIPTION OF THE DRAWINGS

FIG. 2 shows a feature map of the full-length cynoTLR3 peptide chain (SEQ ID NO: 2).

SUMMARY OF THE INVENTION

Figure 1:
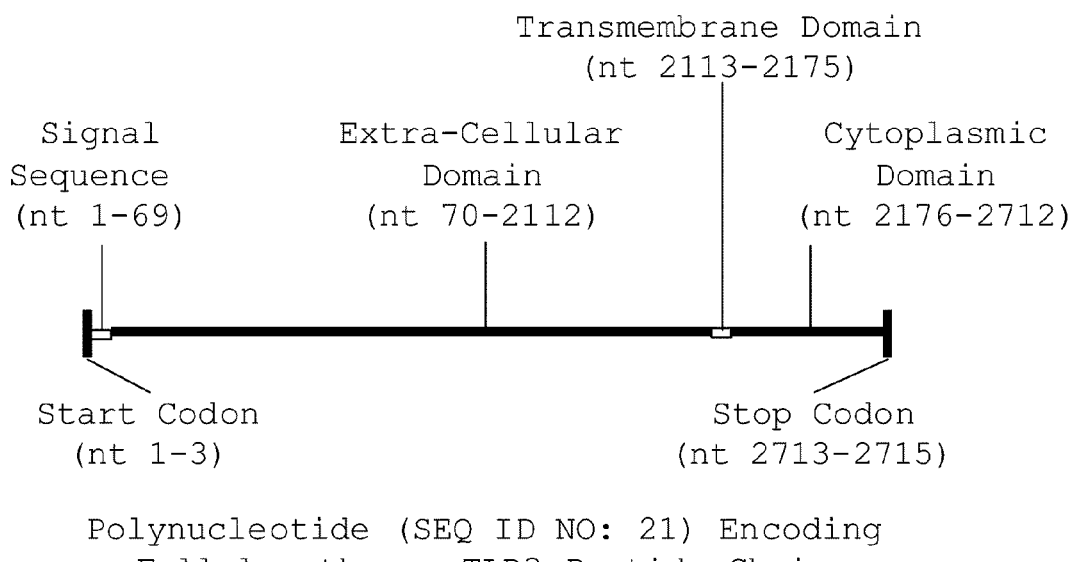
FIG. 1 shows a feature map of the polynucleotide (SEQ ID NO: 21) coding sequence encoding the full-length cynoTLR3 peptide chain.

One aspect of the invention is an isolated polynucleotide comprising a polynucleotide having the sequence shown in SEQ ID NO: 1 or a complementary sequence thereof.

Another aspect of the invention is an isolated polynucleotide comprising a polynucleotide having the sequence shown in SEQ ID NO: 2 or a complementary sequence thereof.

Another aspect of the invention is an isolated polynucleotide comprising a polynucleotide having the sequence shown in SEQ ID NO: 3 or a complementary sequence thereof.

Another aspect of the invention is an isolated polynucleotide comprising a polynucleotide having the sequence shown in SEQ ID NO: 4 or a complementary sequence thereof.

Another aspect of the invention is an isolated polynucleotide comprising a polynucleotide having the sequence shown in SEQ ID NO: 5 or a complementary sequence thereof.

Another aspect of the invention is a vector comprising an isolated polynucleotide having a sequence selected from the group consisting of a sequence show in SEQ ID NO: 1, 2, 3, 4, 5, 6, and 7.

Another aspect of the invention is an isolated peptide chain comprising a peptide chain having the sequence shown in SEQ ID NO: 8.

Another aspect of the invention is an isolated peptide chain comprising a peptide chain having the sequence shown in SEQ ID NO: 9.

Another aspect of the invention is an isolated peptide chain comprising a peptide chain having the sequence shown in SEQ ID NO: 10.

Another aspect of the invention is an isolated peptide chain comprising a peptide chain having the sequence shown in SEQ ID NO: 11.

Another aspect of the invention is a method for expressing a peptide chain comprising the steps of providing an RNA coding for at least one polypeptide comprising the sequence shown in SEQ ID NO: 8, SEQ ID NO: 9, SEQ ID NO: 10 or SEQ ID NO: 11; providing the components of a cell free expression system; initiating cell free expression from the RNA provided; and confirming expression of at least one peptide chain comprising the sequence shown in SEQ ID NO: 8, SEQ ID NO: 9, SEQ ID NO: 10 or SEQ ID NO: 11.

Another aspect of the invention is a method for determining if a TLR3 therapeutic causes adverse events comprising providing a TLR3 therapeutic, a first Cynomolgus monkey, and a second Cynomolgus monkey; administering the TLR3 therapeutic to the first Cynomolgus monkey; and determining whether the first Cynomolgus monkey is presenting a deleterious symptom relative to the second monkey, where presentation of a deleterious symptom by the first Cynomolgus monkey shows the TLR3 therapeutic is unsafe and a lack of presentation of a deleterious symptom by the first Cynomolgus monkey shows the TLR3 therapeutic is safe.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The present invention provides isolated Cynomolgus monkey (*Macaca fascicularis*) Toll-Like Receptor 3 (cynoTLR3) polynucleotides, vectors comprising these polynucleotides, isolated host cells, peptide chains obtainable from expression of these polynucleotides, methods for expressing the peptide chains of the invention, and uses of these are disclosed.

TLR3s are members of the Toll-like receptor family of pathogen associated molecular pattern (PAMP) recognition receptors. TLR3s are activated by binding of double-stranded RNAs. Double stranded RNAs (dsRNAs) are produced during viral infection, infection by other organisms and by cell injury or necrosis. See e.g. Kariko et al., 279 *J. Biol. Chem.* 12542 (2004); see also Alexopoulou et al., 413 *Nature* 732 (2001)). Activation of TLR3s in response to the detection of viral infection associated dsRNA or dsRNAs produced by other sources results in activation of NF-kB to increase production of type I interferons that have antiviral and immune system stimulatory functions. See e.g. Takeda and Akira, 5 *Cell. Micro.* 143, 144 (2003). The result of TLR3 activation in the context of a viral infection is stimulation of the antiviral defenses of the innate and humoral immune systems. For example, the human TLR3 peptide chain is expressed in the central nervous system (CNS), where it is required to control infection by the HSV-1 virus, which spreads from the epithelium to the central nervous system via cranial nerves to cause herpes simplex encephalitis in TLR3 deficient patients. See e.g. Zhang et al., 317 *Science* 1522 (2007). In other contexts, however, human TLR3 peptide chain activation results in inflammatory responses associated with pathological conditions such as, for example, primary biliary cirrhosis of liver tissues. See e.g. Takii et al., 85 *Lab. Invest.* 836 (2005). Importantly, the full-length cynoTLR3 peptide chain sequence (SEQ ID NO: 10) is 95.7% identical, and 96.8% similar to the well-characterized human TLR3 peptide chain (SEQ ID NO: 13).

The compositions and methods of the invention can be used for a variety of specific applications. The polynucleotides and vectors of the invention are useful because they encode Cynomolgus monkey (*Macaca fascicularis*) TLR3 (cynoTLR3) peptide chains and can be used to express these peptide chains. These cynoTLR3 peptide chains are, in turn, useful because they can be used to increase or control antiviral responses after exposure to dsRNA or other TLR3 ligands when they are recombinantly over expressed or introduced by other means into a host animal or tissue.

Peptide chains comprising the extracellular domain of cynoTLR3 can also be used as ligand sink type antagonists that bind available TLR3 ligands or TLR3 associated proteins necessary for TLR3 activation and thus control TLR3 activity. cynoTLR3 peptide chains can also be used to generate therapeutic antibodies for the positive or negative modulation of the activity of cynoTLR3 or TLR3s from other sources. This is desirable because agonist therapeutic antibodies can be used to increase activation of cynoTLR3 or other TLR3s to help control infections while antagonist therapeutic antibodies can be used to decrease activation of cynoTLR3 or other TLR3s to help control pathological conditions associated with TLR3 receptor activation mediated inflammatory responses. cynoTLR3 peptide chains can also be used in in vitro or in vivo assays to identify other therapeutics such as small molecules capable of modulating the activity of cynoTLR3 or other TLR3s. The methods of expression disclosed are useful because these methods permit the expression of cynoTLR3 peptides. Other methods disclosed are useful because they permit a safety assessment of a TLR3 therapeutic.

The term "polynucleotide" means a molecule comprising a chain of nucleobases covalently linked by a sugar-phosphate backbone or other equivalent covalent chemistry. Double and single stranded DNAs and RNAs are typical examples of polynucleotides.

The term "complementary sequence" means a second isolated polynucleotide sequence that is antiparallel to a first isolated polynucleotide sequence and that comprises nucleobases complementary to the nucleobases in the first polynucleotide sequence. Typically, such "complementary sequences" are capable of forming a double stranded polynucleotide molecule such as double stranded DNA or double stranded RNA when combined under appropriate conditions with the first isolated polynucleotide sequence.

The term "vector" means a polynucleotide capable of being duplicated within a biological system or that can be moved between such systems. Vector polynucleotides typically contain elements, such as origins of replication or selection markers, that function to facilitate the duplication or maintenance of these polynucleotides in a biological system. Examples of such biological systems may include cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a peptide chain encoded by a polynucleotide sequence present in the expression vector.

The term "peptide chain" means a molecule that comprises at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "antibody" means immunoglobulin or antibody molecules comprising polyclonal antibodies, monoclonal antibodies including murine, human, humanized and chimeric monoclonal antibodies and antibody fragments, portions, or variants. Antibodies are secreted proteins constitutively expressed and secreted by plasma cells. Antibodies may be of any isotype such as IgG, IgA, or IgM and may comprise antibody fragments such as Fab' fragments. An antibody may also be a bispecific antibody that specifically binds two different peptide chain epitopes.

Antibodies can be produced using plasma cells immortalized by standard methods such as hybridoma generation or by transfection of antibody heavy and/or light chain genes into an immortalized B cell such as a myeloma cell or other cell types, such as Chinese hamster ovary (CHO) cells, plant cells and insect cells.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., 256 *Nature* 495 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., 86 *Proc. Natl. Acad. Sci.* (*USA*) 10029 (1989) and Hodgson et al., 9 *Bio/Technology* 421 (1991).

Exemplary human framework sequences useful for humanization are disclosed at, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGN-MENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; and Kabat et al., Sequences of Proteins of Immunological Interest, U.S. Dept. Health (1987), each entirely incorporated herein by reference.

Fully human mAbs lacking any non-human sequences can be prepared from human immunoglobulin transgenic mice by techniques referenced in, e.g., Lonberg et al., 368 *Nature* 856 (1994); Fishwild et al., 14 *Nature Biotech.* 845 (1996) and Mendez et al., 15 *Nature Genetics* 146 (1997). Human mAbs can also be prepared and optimized from phage display libraries by techniques referenced in, e.g., Knappik et al., 296 *J. Mol. Biol.* 57 (2000) and Krebs et al., 254 *J. Immunol. Meth.* 67 (2001).

An antibody molecule or preparation "specifically binds" a given antigen when it binds this antigen with higher affinity and in a specific, as opposed to non-specific fashion, relative to a second non-identical antigen. Stated differently, the "specific binding" of an antibody molecule or preparation can be used to distinguish between two different peptide chains.

A "fragment" is a peptide chain having an amino acid sequence that comprises a portion, but not all, of any amino acid sequence of any peptide chain of the invention. Fragments can include, for example, truncated peptide chain having a portion of an amino acid sequence corresponding to a signal peptide, extracellular domain, transmembrane domain, or cytoplasmic domain, or variants thereof, such as a continuous series of residues that includes a heterologous amino- and/or carboxy-terminal amino acid sequence. Degradation forms of the peptide chains of the invention produced by, or in, a host cell are also included. Other exemplary fragments are characterized by structural or functional attributes such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions and high antigenic index regions. Importantly, the peptide chains of the invention can be used or provided as fragments.

A "variant peptide chain" is a second peptide chain in which amino acid substitutions, insertions, deletions or combinations thereof have been made relative to a first peptide chain. Naturally occurring, modified or atypical amino acids can be used for substitutions and insertions. The peptide chains described by SEQ ID NO: 8 and SEQ ID NO: 9 are exemplary variant peptide chains relative to the peptide chain having the amino acid sequence shown in SEQ ID NO: 11.

A "variant polynucleotide" is a second polynucleotide in which nucleic acid residue substitutions, insertions, deletions, or combinations thereof have been made relative to a first polynucleotide sequence. Naturally occurring or modified nucleobases can be used for substitutions and deletions. The polynucleotides described by SEQ ID NO: 1, SEQ ID NO: 2, SEQ ID NO: 3, and SEQ ID NO: 5 are exemplary variant polynucleotides relative to the polynucleotide having the amino acid sequence shown in SEQ ID NO: 4.

The term "TLR3 therapeutic" means a molecule or preparation that is believed to provide a therapeutic benefit and is believed to provide that therapeutic benefit, in part, through the activity of a TLR3. Such TLR3s may comprise the peptide chains of the invention. Examples of TLR3 therapeutics include known TLR3 ligands such as dsRNA or poly(I:C) which bind and activate TLR3s to produce the therapeutic benefits of increased antiviral activity and immune system stimulation.

The term "deleterious symptom" means any symptom presented by an animal that indicates harm to the animal has occurred.

One aspect of the invention is an isolated polynucleotide comprising a polynucleotide having the sequence shown in SEQ ID NO: 1 or a complementary sequence thereof. The polynucleotide sequence shown in SEQ ID NO: 1 encodes a peptide chain comprising the predicted mature form of the cynoTLR3 extracellular domain.

The polynucleotides of the invention may be produced by chemical synthesis such as solid phase polynucleotide synthesis on an automated polynucleotide synthesizer. Alternatively, the polynucleotides of the invention may be produced by other techniques such a PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide, as described in Gentz et al., 86 *Proc. Natl. Acad. Sci.* (*USA*) 821 (1989) or the HA peptide tag as described in Wilson et al., 37 *Cell* 767 (1984) which facilitate the purification of fused polypeptides.

Another aspect of the invention is an isolated polynucleotide comprising a polynucleotide having the sequence shown in SEQ ID NO: 2 or a complementary sequence thereof. The polynucleotide sequence shown in SEQ ID NO: 2 encodes a peptide chain comprising the predicted cynoTLR3 signal peptide without its amino terminal methionine residue, and the extracellular domain.

Another aspect of the invention is an isolated polynucleotide comprising a polynucleotide having the sequence shown in SEQ ID NO: 3 or a complementary sequence thereof. The polynucleotide sequence shown in SEQ ID NO: 3 encodes a peptide chain comprising the predicted mature form of the cynoTLR3 extracellular domain, the transmembrane domain, and the cytoplasmic domain.

Another aspect of the invention is an isolated polynucleotide comprising a polynucleotide having the sequence shown in SEQ ID NO: 4 or a complementary sequence thereof. The polynucleotide sequence shown in SEQ ID NO: 4 encodes a peptide chain comprising the predicted cynoTLR3 signal peptide without its amino terminal methionine residue, the extracellular domain, the transmembrane domain, and the cytoplasmic domain.

Another aspect of the invention is an isolated polynucleotide comprising a polynucleotide having the sequence shown in SEQ ID NO: 5 or a complementary sequence thereof. The polynucleotide sequence shown in SEQ ID NO: 5 is a nucleic acid with 5' and 3' sequences flanking an open reading frame encoding a peptide chain comprising full-length cynoTLR3.

Another aspect of the invention is a vector comprising an isolated polynucleotide having a sequence selected from the group consisting of a sequence show in SEQ ID NO: 1, 2, 3, 4, 5, 6, and 7. The polynucleotide sequence shown in SEQ ID NO: 6 is a polynucleotide (DNA) expression vector designated p4078 that encodes a peptide chain comprising full-length cynoTLR3. The polynucleotide sequence shown in SEQ ID NO: 7 is a polynucleotide (DNA) expression vector designated p4037 that encodes a peptide chain comprising the predicted cynoTLR3 signal sequence with an amino terminal methionine residue, and extracellular domain fused via a flexible glycine and serine link to six amino terminal histidine amino acid residue tags. The polynucleotides shown in SEQ ID NO: 1, 2, 3, 4, and 5 are described above.

The vectors of the invention are useful for maintaining polynucleotides, duplicating polynucleotides, or driving expression of a peptide chain encoded by a vector of the invention in a biological systems—including reconstituted biological systems.

Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids.

The vectors of the invention can be formulated in microparticles, with adjuvants, with lipid, buffer or other excipients as appropriate for a particular application.

In one embodiment of the invention the vector is an expression vector.

Expression vectors typically comprise nucleic acid sequence elements that can control, regulate, cause or permit expression of a peptide chain encoded by such a vector. Such elements may comprise transcriptional enhancer binding sites, RNA polymerase initiation sites, ribosome binding sites, and other sites that facilitate the expression of encoded peptide chains in a given expression system. Such expression systems may be cell based, or cell free systems well known in the art. Nucleic acid sequence elements and parent vector sequences suitable for use in the expression of encoded peptide chains are also well known in the art.

Another embodiment of the invention is an isolated host cell comprising a vector of the invention.

An exemplary plasmid derived expression vector useful for expression of the polypeptides of the invention comprises an *E. coli* origin of replication, an aph(3')-1a kanamycin resistance gene, HCMV immediate early promoter with intron A, a synthetic polyA sequence and a bovine growth hormone terminator. Another exemplary plasmid derived expression vector comprises an *E. coli* origin of replication, an ant(4')-1a kanamycin resistance gene, Rous sarcoma virus long terminal repeat sequences, HCMV immediate early promoter and an SV40 late polyA sequence.

Representative host cell examples include Archaea cells; bacterial cells such as Streptococci, Staphylococci, Enterococci, *E. coli, Streptomyces*, cyanobacteria, *B. subtilis* and *S. aureus*; fungal cells such as *Kluveromyces, Saccharomyces, Basidomycete, Candida albicans* or *Aspergillus*; insect cells such as *Drosophila* S2 and *Spodoptera* Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art from laboratory manuals such as Davis et al., *Basic Methods in Molecular Biology*, $2^{nd}$ ed., Appleton & Lange, Norwalk, Conn. (1994) and Sambrook et al., *Molecular Cloning: A Laboratory Manual*, $3^{rd}$ ed., Cold Spring Harbor Laboratory Press, Cold Spring Harbor, N.Y. (2001). These methods include calcium phosphate transfection, DEAE-Dextran mediated transfection, microinjection, cationic lipid-mediated transfection, electroporation, transduction, scrape loading, ballistic introduction and infection.

Another aspect of the invention is an isolated peptide chain comprising a peptide chain having the sequence shown in SEQ ID NO: 8. SEQ ID NO: 8 is a peptide chain comprising the predicted mature form of the cynoTLR3 extracellular domain.

The peptide chains of the invention may be produced by chemical synthesis, such as solid phase peptide syntheses, on an automated peptide synthesizer. Alternatively, the peptide chains of the invention can be obtained from polynucleotides encoding these peptide chains by the use of cell free expression systems such as reticulocyte lystate based expression systems, wheat germ extract based expression systems, and *Escherichia coli* extract based expression systems. The peptide chains of the invention can also be obtained by expression and isolation from cells harboring a nucleic acid sequence of the invention by techniques well known in the art, such as recombinant expression of easily isolated affinity labeled peptide chains. Those skilled in the art will recognize other techniques for obtaining the peptide chains of the invention.

The peptide chains of the invention may comprise fusion peptide chains comprising a peptide chain of the invention fused with second peptide chain. Such second peptide chains may be leader or secretory signal sequences, a pre- or pro- or prepro-protein sequence, as well as naturally occurring, or partially synthetic sequences derived in part from a naturally occurring sequence or an entirely synthetic sequence. Secretory signal or leader peptide chain sequences may be selected to direct secretion of the peptide chains of the invention into the lumen of the endoplasmic reticulum or extracellular environment; such peptide chain sequences may be heterologous or endogenous to any peptide chain from a Cynomologus monkey or comprise hybrids of these.

The peptide chains of the invention can also be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the peptide chains of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected.

The peptide chains and nucleic acids of the invention, can also be provided in the form of a pharmaceutical preparation, such as a vaccine for eliciting an immune response, that can be provided in unit dose forms. The appropriate therapeutically effective dose can be determined readily by those of skill in the art. A determined dose may, if necessary, be repeated at appropriate time intervals selected as appropriate by a physician or other person skilled in the relevant art (e.g. nurse, veterinarian, or veterinary technician) during the treatment period.

The peptide chains of the invention can be lyophilized for storage and reconstituted in a suitable carrier prior to use. This technique has been shown to be effective with conventional protein preparations. Lyophilization and reconstitution techniques are well known in the art.

Another aspect of the invention is an isolated peptide chain comprising a peptide chain having the sequence shown in SEQ ID NO: 9. SEQ ID NO: 9 is a peptide chain comprising the predicted cynoTLR3 signal peptide without its amino terminal methionine residue, and the extracellular domain.

Another aspect of the invention is an isolated peptide chain comprising a peptide chain having the sequence shown in SEQ ID NO: 10. SEQ ID NO: 10 is a peptide chain comprising the predicted mature form of the cynoTLR3 extracellular domain, the transmembrane domain, and the cytoplasmic domain.

Another aspect of the invention is an isolated peptide chain comprising a peptide chain having the sequence shown in SEQ ID NO: 11. SEQ ID NO: 11 is a peptide chain comprising the predicted cynoTLR3 signal peptide without its amino terminal methionine residue, the extracellular domain, the transmembrane domain, and the cytoplasmic domain.

Another embodiment of the invention is a method for expressing a peptide chain comprising the steps of providing a host cell of the invention; culturing the host cell under conditions sufficient for the expression of at least one peptide chain comprising the sequence shown in SEQ ID NO: 8, SEQ ID NO: 9, SEQ ID NO: 10 or SEQ ID NO: 11; and confirming expression of at least one peptide chain comprising the sequence shown in SEQ ID NO: 8, SEQ ID NO: 9, SEQ ID NO: 10 or SEQ ID NO: 11.

Host cells can be cultured under any conditions suitable for maintaining or propagating a given type of host cell and sufficient for expressing a peptide chain. Culture conditions, media, and related methods sufficient for the expression of peptide chains are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a peptide chain can be confirmed using a variety of different techniques well known in the art. For example, expression of a peptide chain can be confirmed using detection reagents, such as antibodies or receptor ligands, specific for an expressed peptide chain. Antibodies that specifically bind to the cynoTLR3 peptide chains of the invention are one example of such reagents. TLR3 receptor ligands such as dsRNA or poly(I:C) that bind TLR3 are another example of such reagents. Detection reagents may be detectably labeled by conjugation or incorporation of a radiolabel, fluorophore, chromophore or other detectable molecule to, or into, the detection reagent.

Alternatively, the expression of a cynoTLR3 peptide chain of the invention can be confirmed by assaying for a biological activity associated with activation of TLR3s, such as activation of NF-kB or increased production of type I interferons. Such assays may also utilize reporter gene constructs responsive to TLR3 activation.

Peptide chain expression can also be confirmed by identification of a peptide chain with the physical characteristics of a peptide chain of the invention in a preparation of peptide chains. For example, SDS-PAGE techniques and other well-known protein characterization techniques utilizing criteria such as, for example, protein molecular weight or isoelectric point can be used to confirm expression of the peptide chains of the invention. Protein purification techniques such as ammonium sulfate or ethanol precipitation, acid extraction, high-performance liquid chromatography, anion or cation exchange chromatography, phosphocellulose chromatography, hydrophobic interaction chromatography, affinity chromatography, hydroxyapatite chromatography and lectin chromatography can also be used to confirm expression of a peptide chain of the invention.

Importantly, in the methods of the invention the peptide chain expressed need not be isolated. Consequently, expression of a peptide chain may be confirmed to have occurred on, or in, a cell, or in a mixture of peptide chains for example. Flow cytometry based techniques such as fluorescence activated cell sorting (FACS) may also be used, when appropriate, to confirm expression of a peptide chain by a cell. As discussed above peptide chain expression may be confirmed using any suitable technique known in the art.

Another embodiment of the invention is a method for expressing a peptide chain comprising the steps of providing a polynucleotide of the invention capable of being transcribed into an RNA coding for at least one peptide chain comprising the sequence shown in SEQ ID NO: 8, SEQ ID NO: 9, SEQ ID NO: 10 or SEQ ID NO: 11; providing the components of a cell free expression system; initiating cell free expression from the polynucleotide provided; and confirming expression of at least one peptide chain comprising the sequence shown in SEQ ID NO: 8, SEQ ID NO: 9, SEQ ID NO: 10 or SEQ ID NO: 11.

Techniques for transcribing a polynucleotide into an RNA, obtaining an RNA coding for a peptide chain, or initiating cell free expression are well known in the art and reagent kits for accomplishing these steps are commercially available from a variety of sources.

In another embodiment of the method of the invention the cell free expression system is selected from the group consisting of a reticulocyte lystate based expression system, a wheat germ extract based expression system, and an *Escherichia coli* extract based expression system.

Another embodiment of the invention is a method for expressing a peptide chain comprising the steps of providing an RNA coding for at least one peptide chain comprising the sequence shown in SEQ ID NO: 8, SEQ ID NO: 9, SEQ ID NO: 10 or SEQ ID NO: 11; providing the components of a cell free expression system; initiating cell free expression from the RNA provided; confirming expression of at least one peptide chain comprising the sequence shown in SEQ ID NO: 8, SEQ ID NO: 9, SEQ ID NO: 10 or SEQ ID NO: 11.

In another embodiment of the method of the invention the cell free expression system is selected from the group consisting of a reticulocyte lystate based expression system, a wheat germ extract based expression system, and an *Escherichia coli* extract based expression system.

Another embodiment of the invention is a peptide chain produced by the methods of invention. Such peptide chains may comprise post-translational modifications including glycosylation or phosphorylation for example. Such peptide chains may also comprise alternative peptide chain forms such as splice variants, truncated forms, or proteolytically modified forms.

Another embodiment of the invention is an antibody that specifically binds a peptide chain of the invention. The peptide chains of the invention can be used to produce polyclonal or monoclonal antibodies against cynoTLR3. Techniques for making murine, chimeric, humanized and fully human monoclonal antibodies using protein or nucleic acid immunization are routine and well known to those skilled in the art. Additional discussion and description of such techniques can be found above.

Another embodiment of the invention is a monoclonal antibody that specifically binds a peptide chain of the invention.

Another aspect of the invention is a method for determining if a TLR3 therapeutic is safe or unsafe comprising providing a TLR3 therapeutic, a first Cynomolgus monkey, and a second Cynomolgus monkey; administering the TLR3 therapeutic to the first Cynomolgus monkey; and determining whether the first Cynomolgus monkey is presenting a deleterious symptom relative to the second monkey, where presentation of a deleterious symptom by the first Cynomolgus monkey shows the TLR3 therapeutic is unsafe and a lack of presentation of a deleterious symptom by the first Cynomolgus monkey shows the TLR3 therapeutic is safe.

In the methods of the invention the first and second Cynomolgus monkey provided should be equivalent with regard to the presentation of deleterious symptoms. Stated differently both animals should be presenting either no deleterious symptoms or the same deleterious symptoms when they are provided.

In the methods of the invention TLR3 therapeutics can be administered by any route appropriate such as parenterally, subcutaneously, intravenously, etc. Examples of TLR3 therapeutics suitable for use in the method of the invention include, for example, known TLR3 ligands such as dsRNA or poly(I:C) and peptide chains such as those comprising the TLR3 extracellular domain.

In the methods of the invention the determination of whether the first Cynomolgous monkey is presenting a deleterious symptom relative to the second Cynomolgous monkey is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, infections and the like.

In one embodiment of the method of the invention the TLR3 therapeutic is an antibody.

The present invention will now be described with reference to the following specific, non-limiting examples.

Example 1

Isolation, Cloning and Sequencing of Polynucleotides Encoding Full-Length Cynomolgus Monkey Toll-Like Receptor 3 (cynoTLR3)

RNA was purified from Cynomolgus monkey peripheral blood mononuclear cells (PBMC) using TRIZOL® reagent (Invitrogen, Carlsbad, Calif.) according to the manufacturer's instructions. Reverse transcription reactions were carried out using SUPERSCRIPT II REVERSE TRANSCRIPTASE® kit and were primed using an oligo-dT primer. Primers for initial PCR cloning were designed based on the sequence of the polynucleotide encoding the human TLR3 peptide chain. PCR for the cloning of a polynucleotide (SEQ ID NO: 5) encoding the full-length cynoTLR3 peptide chain (SEQ ID NO: 11) was then performed using the 2535 primer (SEQ ID NO: 14) and 2664 primer (SEQ ID NO: 15). PCR was performed using 100 ng of each primer with 100 ng of cDNA template under the following conditions: 30 cycles of 94° C. 30 seconds, 60° C. 1 minute, 68° C. 1 minute, followed by one cycle of 68° C. for 5 minutes. PCR reaction products were analyzed on agarose gels, and revealed a polynucleotide band of approximately 2700 bp corresponding to the PCR cloned polynucleotide was obtained. Cloned PCR products were purified using QIAQUICK® PCR purification (Qiagen, Valencia, Calif.). PCR products were cloned into a pCR4 TOPO TA® vector to obtain sequence between the 2535 primer (SEQ ID NO: 14) and 2664 primer (SEQ ID NO: 15) for the approximately 2700 bp PCR product.

Sequence masked by the 2535 primer (SEQ ID NO: 14) and 2664 primer (SEQ ID NO: 15) from the approximately 2700 bp PCR product was cloned via the 5' and 3'RACE (Rapid Amplification of cDNA Ends) methods. This was accomplished by first designing the cynoTL3 cDNA specific 2589 primer (SEQ ID NO: 17), 2590 primer (SEQ ID NO: 18), and 2625 primer (SEQ ID NO: 19) using the cynoTLR3 sequence obtained as described above. 3' primers, placed about 150 to 250 bp downstream of the initiation site, was designed to pair with a 5'GENERACER® primer for amplification, cloning and sequencing of the 5' end of the full-length polynucleotide cDNA encoding cynoTLR3. 5' primers, placed about 150 to 250 bp upstream of the termination site, was designed to pair with a 3'GENERACER® primer for amplification, cloning and sequencing of the 3' end of the full-length polynucleotide cDNA encoding cynoTLR3. The PCR products obtained from these amplifications were then cloned into pCR4 TOPO TA® vector and 5' untranslated sequence, amino-terminal coding sequence, carboxy-terminal coding sequence, and 3' untranslated sequence were obtained from the polynucleotides. Primers used to obtain additional sequence had the sequences shown in SEQ ID NO: 17, SEQ ID NO: 18, and SEQ ID NO: 19. Multiple sequence alignment of the sequences obtained was then performed and a polynucleotide (SEQ ID NO: 5) comprising 5' untranslated sequence, a coding sequence encoding the full-length cynoTLR peptide chain (SEQ ID NO: 20), and 3' untranslated sequence was obtained.

Sequence analysis was then performed using Vector NTI v9.0.0 software (Invitrogen Corp., Carlsbad, Calif.). Domains identified in the full-length cynoTLR3 peptide chain are encoded by the cloned polynucleotide (SEQ ID NO: 5) shown in FIG. 1 and FIG. 2. The amino-terminal methionine is encoded by nucleotide residues 1-3 of SEQ ID NO: 21 and corresponds to amino acid residue 1 of SEQ ID NO: 20. The signal peptide is encoded by nucleotide residues 1-69 of SEQ ID NO: 21 and corresponds to amino acid residues 1-23 of SEQ ID NO: 20. The extracellular domain is encoded by nucleotide residues 70-2112 of SEQ ID NO: 21 and corresponds to amino acid residues 24-704 of SEQ ID NO: 20. The transmembrane domain is encoded by nucleotide residues 2113-2175 of SEQ ID NO: 21 and corresponds to amino acid residues 705-725 of SEQ ID NO: 20. The cytoplasmic domain is encoded by nucleotide residues 2176-2712 of SEQ ID NO: 21 and corresponds to amino acid residues 726-904 of SEQ ID NO: 20. The stop codon is encoded by nucleotide residues 2713-2715 of SEQ ID NO: 21.

Multiple sequence alignment analyses were performed using the default settings of the CLUSTALW algorithm employed by the AlignX module of the Vector NTI v9.0.0 software. The full-length polynucleotide coding sequence encoding cynoTLR3 (nucleotide residues 1-2712 of SEQ ID NO: 21) was found to be 96.8% identical to the full-length polynucleotide coding sequence (nucleotide residues 1-2715 of SEQ ID NO: 12) encoding the well characterized full-length human TLR3 peptide chain. The full-length cynoTLR3 peptide chain (SEQ ID NO: 20) was found to be 95.7% identical to the well characterized full-length human TLR3 peptide chain (SEQ ID NO: 13). The mature form of the cynoTLR3 extracellular domain peptide chain (SEQ ID NO: 1) was found to be 95.4% identical to the extracellular domain of the human TLR3 peptide chain (amino acid residues 24 to 704 of SEQ ID NO: 13).

The full-length polynucleotide coding sequence encoding cynoTLR3 (nucleotide residues 1-2712 of SEQ ID NO: 21) was found to be 99.3% identical to the full-length polynucleotide coding sequence (nucleotide residues 1-2712 of SEQ ID NO: 22) encoding the rhesus monkey TLR3 peptide chain. The full-length cynoTLR3 peptide chain (SEQ ID NO: 20) was found to be 98.5% identical to the rhesus monkey TLR3 peptide chain (SEQ ID NO: 23). The mature form of the cynoTLR3 extracellular domain peptide chain (SEQ ID NO: 1) was found to be 98.2% identical to the extracellular domain of the human TLR3 peptide chain (amino acid residues 24 to 704 of SEQ ID NO: 23). The cloning of the polynucleotide (SEQ ID NO: 22) encoding rhesus monkey TLR3 was reported by Sanghavi and Reinhart. See Sanghavi and Reinhart, 175 *J. Immunol.* 5314 (2005).

Example 2

Expression and Purification of a Peptide Chain Comprising the cynoTLR3 Extracellular Domain A polynucleotide encoding an N-terminal methionine, the cynoTLR3 signal peptide chain, and the cynoTLR3 extracellular domain fused via a flexible glycine and serine link to six amino terminal histidine amino acid residue tags was constructed and cloned into an mammalian expression vector to generate the p4037 expression vector construct (SEQ ID NO: 7). Primer 2523 (SEQ ID NO: 16) was used to facilitate the generation of p4037. HEK293 cells were transiently transfected with p4037 using standard methods. The HEK293 cell line is derived from human embryonic kidney cells. These HEK293 cells were then cultured for six days and the cell culture media was collected. TALON® resin purification to isolate the histidine tagged cynoTLR3 extracellular domain fusion peptide chain encoded by p4037 from the collected media was then conducted as directed by the manufacturer (Clontech Laboratories Inc., Mountain View, Calif.). The eluate from the TALON® resin was then analyzed by SDS-PAGE conducted on non-reduced samples and samples subjected to reducing conditions. SDS-PAGE was followed by Western blotting. Western blots were probed with a histidine tag specific probe. Western blots analysis of both reduced and non-reduced samples revealed that a apparently monomeric protein with an approximate molecular weight of 98 kDal was expressed and isolated. The calculated molecular weight of the cynoTLR3 histidine tagged cynoTLR3 extracellular domain fusion peptide chain encoded by p4037 was approximately 80 kDal which is smaller than the 98 kDal histidine tagged peptide chain detected in the Western blots. However, the peptide chain encoded by p4037 comprises 15 N-linked glycosylation sites, and it is believed post-translational glycosylation is largely responsible for the increased molecular weight of the histidine tagged protein expressed.

The present invention now being fully described, it will be apparent to one of ordinary skill in the art that many changes and modifications can be made thereto without departing from the spirit or scope of the appended claims.

The invention claimed is:

1. An isolated peptide chain comprising the amino acid sequence set forth in SEQ ID NO: 8.

2. An isolated peptide chain comprising the amino acid sequence set forth in SEQ ID NO: 9.

3. An isolated peptide chain comprising the amino acid sequence set forth in SEQ ID NO: 10.

4. An isolated peptide chain comprising the amino acid sequence set forth in SEQ ID NO: 11.

* * * * *

SEQUENCE LISTING

<160> NUMBER OF SEQ ID NOS: 23

<210> SEQ ID NO 1
<211> LENGTH: 2043
<212> TYPE: DNA
<213> ORGANISM: Macaca fascicularis

<400> SEQUENCE: 1

| | | | | | | |
|---|---|---|---|---|---|---|
| tccaccaaca | aatgcactgt | tagccaagaa | gttgctgact | gcagccacct | gaagttaact | 60 |
| caggtacccg | atgatctccc | cacaaacata | acagtgttga | atcttaccca | taatcaactc | 120 |
| agaagattac | cagctgccaa | ttttacaaga | tatagccaac | taactatctt | ggatgtagga | 180 |
| tttaactcca | tctcaaaact | ggagccagaa | ttgtgccaaa | aacttcccat | gttaaaagtt | 240 |
| ttgaacctcc | agcacaatga | gctatctcaa | ctttctgata | aaacttttgc | cttctgcacg | 300 |
| aatttgacgg | aactccatct | catgtccaac | tcaatccaga | aaattaaaaa | taatcccttt | 360 |
| gtaaagcaga | agaatttaat | cacattagat | ctgtctcata | atggcttgtc | atctacaaaa | 420 |
| ttaggaactc | aggttcagct | ggaaaatctc | caagagcttc | tattatcaaa | caataaaatc | 480 |
| caagcgctaa | aaagtgaaga | acttggtatc | cttgccaatt | catctttaaa | aaagttagag | 540 |
| ttgtcatcga | atcaaattaa | agagttttct | ccagggtgtt | ttcacgcaat | tggaagatta | 600 |
| ttgggcctct | ttctgaacaa | tgtccagctg | ggtccccgcc | tcacagagaa | gctatgtttg | 660 |
| gaattagcaa | acacaagcgt | tcggaatctg | tctctgagta | acagccagct | gtccaccacc | 720 |
| agcaatacaa | ctttcttggg | actaaagtgg | acaaacctca | ctatgctcga | tctttcccac | 780 |
| aacaacttaa | atgtgattgg | taacgattcc | tttgtttggc | ttccacatct | agaatatttc | 840 |
| ttcctggagt | ataataatat | acagcatttg | ctctctcact | ctttgcacgg | gcttttcaat | 900 |
| gtgcggtacc | tgaatttgaa | acggtctttt | actaaacaaa | gtatttccct | tgcttcgctc | 960 |
| cccaagattg | atgattttc | ttttcggtgg | ctaacatgtt | tggagcacct | taacatggaa | 1020 |
| gataatgata | tttcaggcat | aaaaagcaat | atgttcacag | gattgataaa | cctgaaatac | 1080 |
| ttaagtctat | ccaactcctt | tacaagtttg | caaactttga | caaatgaaac | atttgtatca | 1140 |
| cttgctcatt | ctcccttaca | catactcaac | ctaaccaaga | ataaaatctc | aaaaatagag | 1200 |
| agtggtgcct | tctcttggtt | gggccaccta | gaagtacttg | acttgggcct | taatgaaatt | 1260 |
| gggcaagaac | tcacaggcca | ggaatggagt | ggtctagaaa | atattttcga | aatctatctt | 1320 |
| tcctacaaca | agtacctgca | actgactaag | aactcctttg | ccttggtccg | aagccttcaa | 1380 |
| cgactgatgc | tccgaagggt | ggcccttaaa | aatgtggatt | gctctccttc | accattccag | 1440 |
| cctcttggta | acctgaccat | tctggatcta | agcaacaaca | acatagccaa | cataaatgat | 1500 |
| gacatgttgg | aaggtcttga | gaaactagaa | attctggatt | tgcagcataa | caacttagca | 1560 |
| cggctctgga | aacacgcaaa | ccctggtggt | cctgtttatt | tcctaaaggg | tctgtctcac | 1620 |
| ctccacatcc | ttaacttgga | gtctaatggc | tttgacgaga | tcccagttga | ggtcttcaag | 1680 |
| gatttatctg | aactaaagat | cattgattta | ggattgaata | atttaaacac | acttccagcg | 1740 |
| tctgtctttg | ataatcaggt | gtctctaaag | tcattgaacc | ttcagaagaa | tctcataaca | 1800 |
| tcagttgaga | agaaggtttt | cggccagct | ttcaggaacc | tgagtaactt | agatatgcgc | 1860 |
| tttaatccct | tgattgcac | atgtgaaagt | attgcctggt | tgttaattg | gattaacaag | 1920 |
| acccacgcca | acatccctga | gctgtcaagc | cactaccttt | gcaacactcc | accccactat | 1980 |

| | |
|---|---|
| catgggttcc cagtgagact ttttgataca tcatcctgca aagacagtgc ccccttttgaa | 2040 |
| ctc | 2043 |

<210> SEQ ID NO 2
<211> LENGTH: 2643
<212> TYPE: DNA
<213> ORGANISM: Macaca fascicularis

<400> SEQUENCE: 2

| | |
|---|---|
| tccaccaaca aatgcactgt tagccaagaa gttgctgact gcagccacct gaagttaact | 60 |
| caggtacccg atgatctccc cacaaacata acagtgttga atcttaccca taatcaactc | 120 |
| agaagattac cagctgccaa ttttacaaga tatagccaac taactatctt ggatgtagga | 180 |
| tttaactcca tctcaaaact ggagccagaa ttgtgccaaa acttcccat gttaaaagtt | 240 |
| ttgaacctcc agcacaatga gctatctcaa cttctgata aaacttttgc cttctgcacg | 300 |
| aatttgacgg aactccatct catgtccaac tcaatccaga aaattaaaaa taatcccttt | 360 |
| gtaaagcaga agaatttaat cacattagat ctgtctcata atggcttgtc atctacaaaa | 420 |
| ttaggaactc aggttcagct ggaaaatctc caagagcttc tattatcaaa caataaaatc | 480 |
| caagcgctaa aaagtgaaga acttggtatc cttgccaatt catctttaaa aaagttagag | 540 |
| ttgtcatcga atcaaattaa agagttttct ccagggtgtt tcacgcaat tggaagatta | 600 |
| ttgggcctct ttctgaacaa tgtccagctg ggtccccgcc tcacagagaa gctatgtttg | 660 |
| gaattagcaa acacaagcgt tcggaatctg tctctgagta acagccagct gtccaccacc | 720 |
| agcaatacaa ctttcttggg actaaagtgg acaaacctca ctatgctcga tcttcccac | 780 |
| aacaacttaa atgtgattgg taacgattcc tttgtttggc ttccacatct agaatatttc | 840 |
| ttcctggagt ataataatat acagcatttg ctctctcact cttttgcacgg cttttcaat | 900 |
| gtgcggtacc tgaatttgaa acggtctttt actaaacaaa gtatttccct tgcttcgctc | 960 |
| cccaagattg atgattttc ttttcggtgg ctaacatgtt tggagcacct taacatggaa | 1020 |
| gataatgata tttcaggcat aaaaagcaat atgttcacag gattgataaa cctgaaatac | 1080 |
| ttaagtctat ccaactcctt tacaagtttg caaactttga caaatgaaac atttgtatca | 1140 |
| cttgctcatt ctcccttaca catactcaac ctaaccaaga ataaaatctc aaaaatagag | 1200 |
| agtggtgcct ctctcttggtt gggccaccta gaagtacttg acttgggcct taatgaaatt | 1260 |
| gggcaagaac tcacaggcca ggaatggagt ggtctagaaa atattttcga aatctatctt | 1320 |
| tcctacaaca agtacctgca actgactaag aactccttg ccttggtccg aagccttcaa | 1380 |
| cgactgatgc tccgaagggt ggcccttaaa aatgtggatt gctctccttc accattccag | 1440 |
| cctcttggta acctgaccat tctggatcta agcaacaaca acatagccaa cataaatgat | 1500 |
| gacatgttgg aaggtcttga gaaactagaa attctggatt tgcagcataa caacttagca | 1560 |
| cggctctgga acacgcaaa ccctggtggt cctgtttatt tcctaaaggg tctgtctcac | 1620 |
| ctccacatcc ttaacttgga gtctaatggc tttgacgaga tcccagttga ggtcttcaag | 1680 |
| gatttatctg aactaaagat cattgattta ggattgaata atttaaacac acttccagcg | 1740 |
| tctgtctttg ataatcaggt gtctctaaag tcattgaacc ttcagaagaa tctcataaca | 1800 |
| tcagttgaga agaaggtttt cgggccagct ttcaggaacc tgagtaactt agatatgcgc | 1860 |
| tttaatccct tgattgcac atgtgaaagt attgcctggt tgttaattg gattaacaag | 1920 |
| acccacgcca acatccctga gctgtcaagc cactaccttt gcaacactcc accccactat | 1980 |
| catgggttcc cagtgagact ttttgataca tcatcctgca aagacagtgc ccccttttgaa | 2040 |

```
ctcttttttca tgatcaatac cagtatcctg ttgatttttta tctttgttgt acttctcatc    2100
cactttgagg gctggaggat atcttttttac tggaatgttt cagtacatcg agttcttggt    2160
ttcaaagaaa tagacagaca gacagaacag tttgaatatg cagcatatat aattcacgcc    2220
cataaagata aggattgggt ctgggaacat ttctcttcaa tggaaaagga agaccaatct    2280
ctcaaatttt gtctggaaga aagggactttt gaggcaggtg ttttttgaact ggaagcaatt    2340 gttaacagca tcaaaagaag cagaaaaatt atttttatta taacacacca tctattaaaa    2400
gacccattat gcaaaagatt caaggtacat catgccgttc aacaagctat tgaacaaaat    2460
ctggattcca ttatattgat tttccttgag gagattccag attataaact gaaccatgca    2520
ctctgtttgc gaagaggaat gtttaaatct cactgcatct tgaactggcc agttcagaaa    2580
gaacggatag gtgcctttca tcataaactg caagtagcac ttggatccaa aaactcagta    2640
cat                                                                    2643

<210> SEQ ID NO 3
<211> LENGTH: 2643
<212> TYPE: DNA
<213> ORGANISM: Macaca fascicularis

<400> SEQUENCE: 3
tccaccaaca aatgcactgt tagccaagaa gttgctgact gcagccacct gaagttaact      60
caggtacccg atgatctccc cacaaacata acagtgttga atcttaccca taatcaactc     120
agaagattac cagctgccaa ttttacaaga tatagccaac taactatctt ggatgtagga     180
tttaactcca tctcaaaact ggagccagaa ttgtgccaaa acttcccat gttaaaagtt      240 ttgaacctcc agcacaatga gctatctcaa ctttctgata aaacttttgc cttctgcacg     300
aatttgacgg aactccatct catgtccaac tcaatccaga aaattaaaaa taatcccttt     360
gtaaagcaga gaatttaat cacattagat ctgtctcata atggcttgtc atctacaaaa     420
ttaggaactc aggttcagct ggaaaatctc caagagcttc tattatcaaa caataaaatc     480
caagcgctaa aaagtgaaga acttggtatc cttgccaatt catctttaaa aaagttagag     540
ttgtcatcga atcaaattaa agagttttct ccagggtgtt tcacgcaat tggaagatta     600 tgggcctct ttctgaacaa tgtccagctg ggtccccgcc tcacagagaa gctatgtttg     660
gaattagcaa acacaagcgt tcggaatctg tctctgagta acagccagct gtccaccacc     720
agcaatacaa ctttcttggg actaaagtgg acaaacctca ctatgctcga tctttcccac     780
aacaacttaa atgtgattgg taacgattcc tttgtttggc ttccacatct agaatatttc     840
ttcctggagt ataataatat acagcatttg ctctctcact ctttgcacgg cttttttcaat    900 gtgcggtacc tgaatttgaa acggtctttt actaaacaaa gtatttccct tgcttcgctc     960
cccaagattg atgatttttc ttttcggtgg ctaacatgtt tggagcacct taacatggaa    1020
gataatgata tttcaggcat aaaaagcaat atgttcacag gattgataaa cctgaaatac    1080
ttaagtctat ccaactcctt tacaagttg caaactttga caaatgaaac atttgtatca    1140
cttgctcatt ctcccttaca catactcaac ctaaccaaga ataaaatctc aaaaatagag    1200
agtggtgcct tctcttggtt gggccaccta gaagtacttg acttgggcct taatgaaatt    1260
gggcaagaac tcacaggcca ggaatggagt ggtctagaaa atattttcga aatctatctt    1320
tcctacaaca agtacctgca actgactaag aactcctttg ccttggtccg aagccttcaa    1380
cgactgatgc tccgaaggg ggcccttaaa aatgtggatt gctctccttc accattccag    1440
cctcttggta acctgaccat tctggatcta agcaacaaca acatagccaa cataaatgat    1500
```

```
gacatgttgg aaggtcttga gaaactagaa attctggatt tgcagcataa caacttagca   1560
cggctctgga aacacgcaaa ccctggtggt cctgtttatt tcctaaaggg tctgtctcac   1620
ctccacatcc ttaacttgga gtctaatggc tttgacgaga tcccagttga ggtcttcaag   1680
gatttatctg aactaaagat cattgattta ggattgaata atttaaacac acttccagcg   1740
tctgtctttg ataatcaggt gtctctaaag tcattgaacc ttcagaagaa tctcataaca   1800
tcagttgaga agaaggtttt cgggccagct ttcaggaacc tgagtaactt agatatgcgc   1860
tttaatccct ttgattgcac atgtgaaagt attgcctggt tgttaattg gattaacaag    1920 acccacgcca acatccctga gctgtcaagc cactaccttt gcaacactcc accccactat   1980
catgggttcc cagtgagact ttttgataca tcatcctgca aagacagtgc cccctttgaa   2040 ctcttttttca tgatcaatac cagtatcctg ttgatttta tctttgttgt acttctcatc   2100
cactttgagg gctggaggat atcttttac tggaatgttt cagtacatcg agttcttggt    2160
ttcaaagaaa tagacagaca gacagaacag tttgaatatg cagcatatat aattcacgcc   2220
cataaagata aggattgggt ctgggaacat ttctcttcaa tggaaaagga agaccaatct   2280
ctcaaatttt gtctggaaga aagggacttt gaggcaggtg ttttttgaact ggaagcaatt   2340 gttaacagca tcaaaagaag cagaaaaatt attttttatta taacacacca tctattaaaa   2400
gacccattat gcaaaagatt caaggtacat catgccgttc aacaagctat tgaacaaaat   2460
ctggattcca ttatattgat tttccttgag gagattccag attataaact gaaccatgca   2520
ctctgtttgc gaagaggaat gtttaaatct cactgcatct tgaactggcc agttcagaaa   2580
gaacggatag gtgcctttca tcataaactg caagtagcac ttggatccaa aaactcagta   2640
cat                                                                 2643

<210> SEQ ID NO 4
<211> LENGTH: 2709
<212> TYPE: DNA
<213> ORGANISM: Macaca fascicularis

<400> SEQUENCE: 4
agacagactt tgccttatac ctacttttgg tggggacttt tgccctttgg gatgctgtgt     60
gcatcctcca ccaacaaatg cactgttagc caagaagttg ctgactgcag ccacctgaag   120
ttaactcagg tacccgatga tctccccaca aacataacag tgttgaatct tacccataat   180
caactcagaa gattaccagc tgccaatttt acaagatata gccaactaac tatcttggat   240
gtaggattta actccatctc aaaactggag ccagaattgt gccaaaaact tcccatgtta   300
aaagttttga acctccagca caatgagcta tctcaacttt ctgataaaac ttttgccttc   360
tgcacgaatt tgacggaact ccatctcatg tccaactcaa tccagaaaat taaaaataat   420
ccctttgtaa agcagaagaa tttaatcaca ttagatctgt ctcataatgg cttgtcatct   480
acaaaattag gaactcaggt tcagctggaa atctccaag agcttctatt atcaaacaat    540
aaaatccaag cgctaaaaag tgaagaactt ggtatccttg ccaattcatc tttaaaaaag   600
ttagagttgt catcgaatca aattaaagag ttttctccag ggtgttttca cgcaattgga   660
agattattgg gcctcttct gaacaatgtc cagctgggtc ccgcctcac agagaagcta     720 tgtttggaat tagcaaacac aagcgttcgg aatctgtctc tgagtaacag ccagctgtcc   780
accaccagca atacaacttt cttgggacta aagtggacaa acctcactat gctcgatctt   840
tcccacaaca acttaaatgt gattggtaac gattcctttg tttggcttcc acatctagaa   900
tatttcttcc tggagtataa taatatacag catttgctct ctcactcttt gcacgggctt   960
```

| | |
|---|---|
| ttcaatgtgc ggtacctgaa tttgaaacgg tcttttacta aacaaagtat ttcccttgct | 1020 |
| tcgctcccca agattgatga ttttctttt cggtggctaa catgtttgga gcaccttaac | 1080 |
| atggaagata atgatatttc aggcataaaa agcaatatgt tcacaggatt gataaacctg | 1140 |
| aaatacttaa gtctatccaa ctcctttaca agtttgcaaa ctttgacaaa tgaaacattt | 1200 |
| gtatcacttg ctcattctcc cttacacata ctcaacctaa ccaagaataa aatctcaaaa | 1260 |
| atagagagtg gtgccttctc ttggttgggc cacctagaag tacttgactt gggccttaat | 1320 |
| gaaattgggc aagaactcac aggccaggaa tggagtggtc tagaaaatat tttcgaaatc | 1380 |
| tatctttcct acaacaagta cctgcaactg actaagaact cctttgcctt ggtccgaagc | 1440 |
| cttcaacgac tgatgctccg aagggtggcc cttaaaaatg tggattgctc tccttcacca | 1500 |
| ttccagcctc ttggtaacct gaccattctg gatctaagca caacaacat agccaacata | 1560 |
| aatgatgaca tgttggaagg tcttgagaaa ctagaaattc tggatttgca gcataacaac | 1620 |
| ttagcacggc tctggaaaca cgcaaaccct ggtggtcctg tttatttcct aaagggtctg | 1680 |
| tctcacctcc acatccttaa cttggagtct aatggctttg acgagatccc agttgaggtc | 1740 |
| ttcaaggatt tatctgaact aaagatcatt gatttaggat tgaataattt aaacacactt | 1800 |
| ccagcgtctg tctttgataa tcaggtgtct ctaaagtcat tgaaccttca gaagaatctc | 1860 |
| ataacatcag ttgagaagaa ggttttcggg ccagctttca ggaacctgag taacttagat | 1920 |
| atgcgcttta atcccttga ttgcacatgt gaaagtattg cctggtttgt taattggatt | 1980 |
| aacaagaccc acgccaacat ccctgagctg tcaagccact acctttgcaa cactccaccc | 2040 |
| cactatcatg ggttcccagt gagactttt gatacatcat cctgcaaaga cagtgccccc | 2100 |
| tttgaactct ttttcatgat caataccagt atcctgttga ttttatctt tgttgtactt | 2160 |
| ctcatccact ttgagggctg gaggatatct ttttactgga atgtttcagt acatcgagtt | 2220 |
| cttggtttca agaaataga cagacagaca gaacagtttg aatatgcagc atatataatt | 2280 |
| cacgcccata agataagga ttgggtctgg gaacatttct cttcaatgga aaaggaagac | 2340 |
| caatctctca aattttgtct ggaagaaagg gactttgagg caggtgtttt tgaactggaa | 2400 |
| gcaattgtta acagcatcaa agaagcaga aaaattattt ttattataac acaccatcta | 2460 |
| ttaaaagacc cattatgcaa aagattcaag gtacatcatg ccgttcaaca agctattgaa | 2520 |
| caaaatctgg attccattat attgatttc cttgaggaga ttccagatta taaactgaac | 2580 |
| catgcactct gtttgcgaag aggaatgttt aaatctcact gcatcttgaa ctggccagtt | 2640 |
| cagaaagaac ggataggtgc ctttcatcat aaactgcaag tagcacttgg atccaaaaac | 2700 |
| tcagtacat | 2709 |

<210> SEQ ID NO 5
<211> LENGTH: 3036
<212> TYPE: DNA
<213> ORGANISM: Macaca fascicularis

<400> SEQUENCE: 5

| | |
|---|---|
| gccacacatt tccctgatga aatgtctgga tttggactaa agaaaaagga atggccagca | 60 |
| gtcatccaac agaatcatga gacagacttt gccttatacc tacttttggt ggggactttt | 120 |
| gccctttggg atgctgtgtg catcctccac caacaaatgc actgttagcc aagaagttgc | 180 |
| tgactgcagc cacctgaagt taactcaggt acccgatgat ctccccacaa acataacagt | 240 |
| gttgaatctt acccataatc aactcagaag attaccagct gccaattta caagatatag | 300 |
| ccaactaact atcttggatg taggatttaa ctccatctca aaactggagc cagaattgtg | 360 |

```
ccaaaaactt cccatgttaa aagttttgaa cctccagcac aatgagctat ctcaactttc    420
tgataaaact tttgccttct gcacgaattt gacggaactc catctcatgt ccaactcaat    480
ccagaaaatt aaaaataatc cctttgtaaa gcagaagaat ttaatcacat tagatctgtc    540
tcataatggc ttgtcatcta caaaattagg aactcaggtt cagctggaaa atctccaaga    600
gcttctatta tcaaacaata aaatccaagc gctaaaaagt gaagaacttg gtatccttgc    660
caattcatct ttaaaaaagt tagagttgtc atcgaatcaa attaaagagt tttctccagg    720
gtgttttcac gcaattggaa gattattggg cctcttctg aacaatgtcc agctgggtcc    780
ccgcctcaca gagaagctat gtttggaatt agcaaacaca agcgttcgga atctgtctct    840
gagtaacagc cagctgtcca ccaccagcaa tacaactttc ttgggactaa agtggacaaa    900
cctcactatg ctcgatcttt cccacaacaa cttaaatgtg attggtaacg attcctttgt    960
ttggcttcca catctagaat atttcttcct ggagtataat aatatacagc atttgctctc   1020
tcactctttg cacgggcttt tcaatgtgcg gtacctgaat ttgaaacggt cttttactaa   1080
acaaagtatt tcccttgctt cgctccccaa gattgatgat ttttcttttc ggtggctaac   1140
atgtttggag caccttaaca tggaagataa tgatatttca ggcataaaaa gcaatatgtt   1200
cacaggattg ataaacctga atacttaag tctatccaac tcctttacaa gtttgcaaac    1260
tttgacaaat gaaacatttg tatcacttgc tcattctccc ttacacatac tcaacctaac   1320
caagaataaa atctcaaaaa tagagagtgg tgccttctct tggttgggcc acctagaagt   1380
acttgacttg ggccttaatg aaattgggca agaactcaca ggccaggaat ggagtggtct   1440
agaaaatatt ttcgaaatct atctttccta caacaagtac ctgcaactga ctaagaactc   1500
ctttgccttg gtccgaagcc ttcaacgact gatgctccga agggtggccc ttaaaaatgt   1560
ggattgctct ccttcaccat tccagcctct tggtaacctg accattctgg atctaagcaa   1620
caacaacata gccaacataa atgatgacat gttggaaggt cttgagaaac tagaaattct   1680
ggatttgcag cataacaact agcacggct ctggaaacac gcaaaccctg gtggtcctgt    1740
ttatttccta aagggtctgt ctcacctcca catccttaac ttggagtcta atggctttga   1800
cgagatccca gttgaggtct tcaaggattt atctgaacta aagatcattg atttaggatt   1860
gaataattta aacacacttc cagcgtctgt ctttgataat caggtgtctc taaagtcatt   1920
gaaccttcag aagaatctca taacatcagt tgagaagaag gttttcgggc cagctttcag   1980
gaacctgagt aacttagata tgcgctttaa tccctttgat tgcacatgtg aaagtattgc   2040
ctggtttgtt aattggatta acaagaccca cgccaacatc cctgagctgt caagccacta   2100
cctttgcaac actccacccc actatcatgg gttcccagtg agacttttg atacatcatc    2160 ctgcaaagac agtgccccct ttgaactctt tttcatgatc aataccagta tcctgttgat   2220
ttttatcttt gttgtacttc tcatccactt tgagggctgg aggatatctt tttactggaa   2280
tgtttcagta catcgagttc ttggtttcaa agaaatagac agacagacag aacagtttga   2340
atatgcagca tatataattc acgcccataa agataaggat tgggtctggg aacatttctc   2400
ttcaatggaa aaggaagacc aatctctcaa attttgtctg gaagaaaggg actttgaggc   2460
aggtgttttt gaactggaag caattgttaa cagcatcaaa agaagcagaa aaattatttt   2520
tattataaca caccatctat taaaagaccc attatgcaaa agattcaagg tacatcatgc   2580
cgttcaacaa gctattgaac aaaatctgga ttccattata ttgatttttcc ttgaggagat   2640 tccagattat aaaactgaacc atgcactctg tttgcgaaga ggaatgttta atctcactg    2700 catcttgaac tggccagttc agaaagaacg gataggtgcc tttcatcata aactgcaagt   2760
```

| | |
|---|---|
| agcacttgga tccaaaaact cagtacatta aatttattta aatattcaat tagcaaagga | 2820 |
| gaaactttct ctatttaaaa agttccatgg ccaatttaag ttttccataa aggtgttata | 2880 |
| atttgtttat tcatatttgt aagtgattat attctatcac gattatatct cttctaggaa | 2940 |
| aatgtatctc cttatttcag gcctattttt gacaactgac taaattttac ccaaaataaa | 3000 |
| cacagaagca cataaaaaaa aaaaaaaaaa aaaaaa | 3036 |

<210> SEQ ID NO 6
<211> LENGTH: 13857
<212> TYPE: DNA
<213> ORGANISM: Macaca fascicularis

<400> SEQUENCE: 6

| | |
|---|---|
| gttgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtccgcccc ctattgacgt caatgacggt aaatggcccg | 300 |
| cctggcatta tgcccagtac atgaccttac gggactttcc tacttggcag tacatctacg | 360 |
| tattagtcat cgctattacc atggtgatgc ggttttggca gtacaccaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa taaccccgcc ccgttgacgc | 540 |
| aaatgggcgg taggcgtgta cggtgggagg tctatataag cagagctcgt ttagtgaacc | 600 |
| gtcagatcgc ctggagacgc catccacgct gttttgacct ccatagaaga caccgggacc | 660 |
| gatccagcct ccgcggccgg aacggtgca ttggaacgcg gattcccgt gccaagagtg | 720 |
| acgtaagtac cgcctataga gtctataggc ccacctcctt ggcttcttat gcatgctata | 780 |
| ctgtttttgg cttggggtct atacaccccc gcttcctcat gttataggtg atggtatagc | 840 |
| ttagcctata ggtgtgggtt attgaccatt attgaccact cccctattgg tgacgatact | 900 |
| ttccattact aatccataac atggctcttt gccacaactc tctttattgg ctatatgcca | 960 |
| atacactgtc cttcagagac tgacacggac tctgtatttt tacaggatgg ggtctcattt | 1020 |
| attatttaca aattcacata tacaacacca ccgtccccag tgcccgcagc ttttattaaa | 1080 |
| cataacgtgg gatctccacg cgaatctcgg gtacgtgttc cggacatggg ctcttctccg | 1140 |
| gtagcggcgg agcttctaca tccgagccct gctcccatgc ctccagcgac tcatggtcgc | 1200 |
| tcggcagctc cttgctccta acagtggagg ccagacttag gcacagcacg atgcccacca | 1260 |
| ccaccagtgt gccgcacaag gccgtggcgg tagggtatgt gtctgaaaat gagctcgggg | 1320 |
| agcgggcttg caccgctgac gcatttggaa gacttaaggc agcggcagaa gaagatgcag | 1380 |
| gcagctgagt tgttgtgttc tgataagagt cagaggtaac tcccgttgcg gtgctgttaa | 1440 |
| cggtggaggg cagtgtagtc tgagcagtac tcgttgctgc cgcgcgcgcc accagacata | 1500 |
| atagctgaca gactaacaga ctgttccttt ccatgggtct tttctgcagt caccgtcctt | 1560 |
| agatctgtct agaagctggg taccagctgc tagcaagctt gccaccatga dacagacttt | 1620 |
| gccttatacc tactttggt ggggactttt gcccttggg atgctgtgtg catcctccac | 1680 |
| caacaaatgc actgttagcc aagaagttgc tgactgcagc cacctgaagt taactcaggt | 1740 |
| acccgatgat ctccccacaa acataacagt gttgaatctt acccataatc aactcagaag | 1800 |
| attaccagct gccaattta caagatatag ccaactaact atcttggatg taggatttaa | 1860 |

```
ctccatctca aaactggagc cagaattgtg ccaaaaactt cccatgttaa aagttttgaa   1920
cctccagcac aatgagctat ctcaactttc tgataaaact tttgccttct gcacgaattt   1980
gacggaactc catctcatgt ccaactcaat ccagaaaatt aaaaataatc cctttgtaaa   2040
gcagaagaat ttaatcacat tagatctgtc tcataatggc ttgtcatcta caaaattagg   2100
aactcaggtt cagctggaaa atctccaaga gcttctatta tcaaacaata aaatccaagc   2160
gctaaaaagt gaagaacttg gtatccttgc caattcatct ttaaaaaagt tagagttgtc   2220
atcgaatcaa attaaagagt tttctccagg gtgttttcac gcaattggaa gattattggg   2280
cctcttcctg aacaatgtcc agctgggtcc ccgcctcaca gagaagctat gtttggaatt   2340
agcaaacaca agcgttcgga atctgtctct gagtaacagc cagctgtcca ccaccagcaa   2400
tacaactttc ttgggactaa agtggacaaa cctcactatg ctcgatcttt cccacaacaa   2460
cttaaatgtg attggtaacg attcctttgt ttggcttcca catctagaat atttcttcct   2520
ggagtataat aatatacagc atttgctctc tcactctttg cacgggcttt tcaatgtgcg   2580
gtacctgaat ttgaaacggt cttttactaa acaaagtatt tcccttgctt cgctccccaa   2640
gattgatgat ttttcttttc ggtggctaac atgtttggag caccttaaca tggaagataa   2700
tgatatttca ggcataaaaa gcaatatgtt cacaggattg ataaacctga aatacttaag   2760
tctatccaac tccttacaa gtttgcaaac tttgacaaat gaaacatttg tatcacttgc   2820
tcattctccc ttacacatac tcaacctaac caagaataaa atctcaaaaa tagagagtgg   2880
tgccttctct tggttgggcc acctagaagt acttgacttg ggcctaatg aaattgggca   2940 agaactcaca ggccaggaat ggagtggtct agaaaatatt ttcgaaatct atctttccta   3000
caacaagtac ctgcaactga ctaagaactc cttttgccttg gtccgaagcc ttcaacgact   3060
gatgctccga agggtggccc ttaaaaatgt ggattgctct ccttcaccat ccagcctct   3120 tggtaacctg accattctgg atctaagcaa caacaacata gccaacataa atgatgacat   3180
gttggaaggt cttgagaaac tagaaattct ggatttgcag cataacaact tagcacggct   3240
ctggaaacac gcaaaccctg gtggtcctgt ttatttccta aagggtctgt ctcacctcca   3300
catccttaac ttggagtcta atggctttga cgagatccca gttgaggtct tcaaggattt   3360
atctgaacta aagatcattg atttaggatt gaataattta aacacacttc cagcgtctgt   3420
ctttgataat caggtgtctc taaagtcatt gaaccttcag aagaatctca taacatcagt   3480
tgagaagaag gttttcgggc cagctttcag gaacctgagt aacttagata tgcgctttaa   3540
tccctttgat tgcacatgtg aaagtattgc ctggtttgtt aattggatta caagaccca   3600 cgccaacatc cctgagctgt caagccacta cctttgcaac actccacccc actatcatgg   3660
gttcccagtg agactttttg atacatcatc ctgcaaagac agtgcccct ttgaactctt   3720 tttcatgatc aataccagta tcctgttgat ttttatcttt gttgtacttc tcatccactt   3780
tgagggctgg aggatatctt tttactggaa tgtttcagta catcgagttc ttggtttcaa   3840
agaaatagac agacagacag aacagtttga atatgcagca tatataattc acgcccataa   3900
agataaggat tgggtctggg aacatttctc ttcaatggaa aaggaagacc aatctctcaa   3960 atttttgtctg gaagaagggg actttgaggc aggtgttttt gaactggaag caattgttaa   4020
cagcatcaaa agaagcagaa aaattatttt tattataaca caccatctat taaaagaccc   4080
attatgcaaa agattcaagg tacatcatgc cgttcaacaa gctattgaac aaaatctgga   4140
ttccattata ttgattttcc ttgaggagat tccagattat aaactgaacc atgcactctg   4200
tttgcgaaga ggaatgtttta aatctcactg catcttgaac tggccagttc agaaagaacg   4260
```

```
gataggtgcc tttcatcata aactgcaagt agcacttgga tccaaaaact cagtacatta    4320
actcgaggcc ggcaaggccg gatccagaca tgataagata cattgatgag tttggacaaa    4380
ccacaactag aatgcagtga aaaaaatgct ttatttgtga aatttgtgat gctattgctt    4440
tatttgtaac cattataagc tgcaataaac aagttaacaa caacaattgc attcatttta    4500
tgtttcaggt tcaggggagg tgtgggaggt tttttaaaag caagtaaaac ctctacaaat    4560
gtggtatggc tgattatgat ccggctgcct cgcgcgtttc ggtgatgacg tgaaaacct     4620 ctgacacatg cagctcccgg agacggtcac agcttgtctg taagcggatg ccggagcag     4680 acaagcccgt caggcgtcag cgggtgttgg cgggtgtcgg ggcgcagcca tgaggtcgac    4740
tctagaggat cgatgccccg ccccggacga actaaacctg actacgacat ctctgcccct    4800
tcttcgcggg gcagtgcatg taatcccttc agttggttgg tacaacttgc caactgggcc    4860
ctgttccaca tgtgacacgg ggggggacca aacacaaagg ggttctctga ctgtagttga    4920
catccttata aatggatgtg cacatttgcc aacactgagt ggctttcatc ctggagcaga    4980
ctttgcagtc tgtggactgc aacacaacat tgcctttatg tgtaactctt ggctgaagct    5040
cttacaccaa tgctggggga catgtacctc ccaggggccc aggaagacta cgggaggcta    5100
caccaacgtc aatcagaggg gcctgtgtag ctaccgataa gcggaccctc aagagggcat    5160
tagcaatagt gtttataagg ccccccttgtt aaccctaaac gggtagcata tgcttcccgg    5220
gtagtagtat atactatcca gactaaccct aattcaatag catatgttac ccaacgggaa    5280
gcatatgcta tcgaattagg gttagtaaaa gggtcctaag gaacagcgat atctcccacc    5340
ccatgagctg tcacggtttt atttacatgg ggtcaggatt ccacgagggt agtgaaccat    5400
tttagtcaca agggcagtgg ctgaagatca aggagcgggc agtgaactct cctgaatctt    5460
cgcctgcttc ttcattctcc ttcgtttagc taatagaata actgctgagt tgtgaacagt    5520
aaggtgtatg tgaggtgctc gaaaacaagg tttcaggtga cgcccccaga ataaaatttg    5580 gacgggggt tcagtggtgg cattgtgcta tgacaccaat ataaccctca caaacccctt     5640
gggcaataaa tactagtgta ggaatgaaac attctgaata tctttaacaa tagaaatcca    5700
tggggtgggg acaagccgta aagactggat gtccatctca cacgaattta tggctatggg    5760
caacacataa tcctagtgca atatgatact ggggttatta agatgtgtcc caggcaggga    5820
ccaagacagg tgaaccatgt tgttacactc tatttgtaac aagggggaaag agagtggacg    5880 ccgacagcag cggactccac tggttgtctc taacaccccc gaaaattaaa cggggctcca    5940
cgccaatggg gcccataaac aaagacaagt ggccactctt tttttgaaa ttgtggagtg     6000 ggggcacgcg tcagccccca cacgccgccc tgcggttttg gactgtaaaa taagggtgta    6060
ataacttggc tgattgtaac cccgctaacc actgcggtca aaccacttgc ccacaaaacc    6120
actaatggca ccccgggggaa tacctgcata agtaggtggg cgggccaaga taggggcgcg    6180
attgctgcga tctggaggac aaattacaca cacttgcgcc tgagcgccaa gcacagggtt    6240
gttggtcctc atattcacga ggtcgctgag agcacggtgg gctaatgttg ccatgggtag    6300
catatactac ccaaatatct ggatagcata tgctatccta atctatatct ggtagcata    6360 ggctatccta atctatatct gggtagcata tgctatccta atctatatct gggtagtata    6420
tgctatccta atttatatct gggtagcata ggctatccta atctatatct gggtagcata    6480
tgctatccta atctatatct gggtagtata tgctatccta atctgtatcc gggtagcata    6540
tgctatccta atagagatta gggtagtata tgctatccta atttatatct gggtagcata    6600
tactacccaa atatctggat agcatatgct atcctaatct atatctgggt agcatatgct    6660
```

```
atcctaatct atatctgggt agcataggct atcctaatct atatctgggt agcatatgct    6720
atcctaatct atatctgggt agtatatgct atcctaattt atatctgggt agcataggct    6780
atcctaatct atatctgggt agcatatgct atcctaatct atatctgggt agtatatgct    6840
atcctaatct gtatccgggt agcatatgct atcctcatgc atatacagtc agcatatgat    6900
acccagtagt agagtgggag tgctatcctt tgcatatgcc gccacctccc aaggggcgt     6960 gaattttcgc tgcttgtcct tttcctgctg gttgctccca ttcttaggtg aatttaagga    7020
ggccaggcta aagccgtcgc atgtctgatt gctcaccagg taaatgtcgc taatgttttc    7080
caacgcgaga aggtgttgag cgcggagctg agtgacgtga caacatgggt atgcccaatt    7140
gccccatgtt gggaggacga aaatggtgac aagacagatg ccagaaaata ccaacagc     7200 acgcatgatg tctactgggg atttattctt tagtgcgggg gaatacacgg cttttaatac    7260
gattgagggc gtctcctaac aagttacatc actcctgccc ttcctcaccc tcatctccat    7320
cacctccttc atctccgtca tctccgtcat cacccctccgc ggcagcccct tccaccatag   7380
gtggaaacca gggaggcaaa tctactccat cgtcaaagct gcacacagtc accctgatat    7440
tgcaggtagg agcgggcttt gtcataacaa ggtccttaat cgcatccttc aaaacctcag    7500
caaatatatg agtttgtaaa aagaccatga ataacagac aatggactcc cttagcgggc     7560
caggttgtgg gccgggtcca ggggccattc caaaggggag acgactcaat ggtgtaagac    7620
gacattgtgg aatagcaagg gcagttcctc gccttaggtt gtaaagggag gtcttactac    7680
ctccatatac gaacacaccg cgacccaag ttccttcgtc ggtagtcctt tctacgtgac      7740
tcctagccag gagagctctt aaaccttctg caatgttctc aaatttcggg ttggaacctc    7800
cttgaccacg atgcttttcc aaaccaccct cctttttgc gccctgcctc catcaccctg     7860
accccggggt ccagtgcttg ggccttctcc tgggtcatct gcggggccct gctctatcgc    7920
tcccgggggc acgtcaggct caccatctgg gccaccttct tggtggtatt caaaataatc    7980
ggcttcccct acagggtgga aaaatggcct tctacctgga gggggcctgc gcggtggaga    8040
cccggatgat gatgactgac tactgggact cctgggcctc ttttctccac gtccacgacc    8100
tctccccctg gctctttcac gacttccccc cctggctctt tcacgtcctc tacccggcg    8160 gcctccacta cctcctcgac cccggcctc actacctcct cgaccccggc tccactgcc      8220 tcctcgaccc cggcctccac ctcctgctcc tgcccctcct gctcctgccc ctcctcctgc    8280 tcctgccct cctgccctc ctgctcctgc ccctcctgcc ctcctgctc ctgcccctcc        8340 tgccctcct gctcctgccc ctcctgcccc tcctcctgct cctgccctc ctgcccctcc       8400 tcctgctcct gccctcctg ccctcctgc tcctgccct cctgcccctc ctgctcctgc        8460
ccctcctgcc cctcctgctc ctgcccctcc tgctcctgcc cctcctgctc ctgcccctcc    8520
tgctcctgcc cctcctgccc ctcctgcccc tcctcctgct cctgcccctc ctgctcctgc    8580
ccctcctgcc cctcctgccc ctcctgctcc tgcccctcct cctgctcctg ccctcctgc     8640 ccctcctgcc cctcctcctg ctcctgcccc tcctgcccct cctgctcctg cccctcctcc    8700
tcctgctcct gccctcctg ccctcctgc cctcctgct ctgcccctcc                   8760 tcctcctgct cctgcccctc ctgctcctgc tgcccctcct gcccctcctg ccctcctcc     8820 tgctcctgcc cctcctcctg ctcctgcccc tcctgcccct cctgcccctc ctgcccctcc    8880
tcctgctcct gccctcctc ctgctcctgc ccctcctgct cctgcccctc ccgctcctgc     8940
tcctgctcct gttccaccgt gggtcccttt gcagccaatg caacttggac gttttttggg   9000
tctccggaca ccatctctat gtcttggccc tgatcctgag ccgcccgggg ctcctggtct    9060
```

```
tccgcctcct cgtcctcgtc ctcttccccg tcctcgtcca tggttatcac cccctcttct   9120
ttgaggtcca ctgccgccgg agccttctgg tccagatgtg tctcccttct ctcctaggcc   9180
atttccaggt cctgtacctg gcccctcgtc agacatgatt cacactaaaa gagatcaata   9240
gacatcttta ttagacgacg ctcagtgaat acagggagtg cagactcctg cccctccaa    9300
cagccccccc accctcatcc ccttcatggt cgctgtcaga cagatccagg tctgaaaatt   9360
ccccatcctc cgaaccatcc tcgtcctcat caccaattac tcgcagcccg gaaaactccc   9420
gctgaacatc ctcaagattt gcgtcctgag cctcaagcca ggcctcaaat tcctcgtccc   9480
cctttttgct ggacggtagg gatggggatt ctcgggaccc ctcctcttcc tcttcaaggt   9540
caccagacag agatgctact ggggcaacgg aagaaaagct gggtgcggcc tgtgaggatc   9600
agcttatcga tgataagctg tcaaacatga gaattcttga agacgaaagg gcctcgtgat   9660
acgcctattt ttataggtta atgtcatgat aataatggtt tcttagacgt caggtggcac   9720
ttttcgggga aatgtgcgcg gaaccccctat ttgtttattt ttctaaatac attcaaatat   9780
gtatccgctc atgagacaat aaccctgata aatgcttcaa taatattgaa aaaggaagag   9840
tatgagtatt caacatttcc gtgtcgccct tattcccttt tttgcggcat tttgccttcc   9900
tgttttttgct cacccagaaa cgctggtgaa agtaaaagat gctgaagatc agttgggtgc   9960
acgagtgggt tacatcgaac tggatctcaa cagcggtaag atccttgaga gttttcgccc  10020
cgaagaacgt tttccaatga tgagcacttt taaagttctg ctatgtggcg cggtattatc  10080
ccgtgttgac gccgggcaag agcaactcgg tcgccgcata cactattctc agaatgactt  10140
ggttgagtac tcaccagtca cagaaaagca tcttacggat ggcatgacag taagagaatt  10200
atgcagtgct gccataacca tgagtgataa cactgcggcc aacttacttc tgacaacgat  10260
cggaggaccg aaggagctaa ccgcttttttt gcacaacatg ggggatcatg taactcgcct  10320
tgatcgttgg gaaccggagc tgaatgaagc cataccaaac gacgagcgtg acaccacgat  10380
gcctgcagca atggcaacaa cgttgcgcaa actattaact ggcgaactac ttactctagc  10440
ttcccggcaa caattaatag actggatgga ggcggataaa gttgcaggac cacttctgcg  10500
ctcggccctt ccggctggct ggtttattgc tgataaatct ggagccggtg agcgtgggtc  10560
tcgcggtatc attgcagcac tggggccaga tggtaagccc tcccgtatcg tagttatcta  10620
cacgacgggg agtcaggcaa ctatggatga acgaaataga cagatcgctg agataggtgc  10680
ctcactgatt aagcattggt aactgtcaga ccaagtttac tcatatatac tttagattga  10740
tttaaaacttt cattttttaat ttaaaaggat ctaggtgaag atcctttttg ataatatcat  10800
gaccaaaatc ccttaacgtg agttttcgtt ccactgagcg tcagaccccg tagaaaagat  10860
caaaggatct tcttgagatc ctttttttct gcgcgtaatc tgctgcttgc aaacaaaaaa   10920
accaccgcta ccagcggtgg tttgtttgcc ggatcaagag ctaccaactc tttttccgaa  10980
ggtaactggc ttcagcagag cgcagatacc aaatactgtc cttctagtgt agccgtagtt  11040
aggccaccac ttcaagaact ctgtagcacc gcctacatac ctcgctctgc taatcctgtt  11100
accagtggct gctgccagtg gcgataagtc gtgtcttacc gggttggact caagacgata  11160
gttaccggat aaggcgcagc ggtcgggctg aacggggggt tcgtgcacac agcccagctt  11220
ggagcgaacg acctacaccg aactgagata cctacagcgt gagctatgag aaagcgccac  11280
gcttcccgaa gggagaaagg cggacaggta tccggtaagc ggcagggtcg gaacaggaga  11340
gcgcacgagg gagcttccag gggaaacgc ctggtatctt tatagtcctg tcgggtttcg  11400
ccacctctga cttgagcgtc gatttttgtg atgctcgtca ggggggcgga gcctatggaa  11460
```

```
aaacgccagc aacgcggcct ttttacggtt cctggccttt tgctggcctt gaagctgtcc    11520
ctgatggtcg tcatctacct gcctggacag catggcctgc aacgcgggca tcccgatgcc    11580
gccggaagcg agaagaatca taatggggaa ggccatccag cctcgcgtcg cgaacgccag    11640
caagacgtag cccagcgcgt cggccccgag atgcgccgcg tgcggctgct ggagatggcg    11700
gacgcgatgg atatgttctg ccaagggttg gtttgcgcat tcacagttct ccgcaagaat    11760
tgattggctc caattcttgg agtggtgaat ccgttagcga ggtgccgccc tgcttcatcc    11820
ccgtggcccg ttgctcgcgt ttgctggcgg tgtccccgga agaaatatat ttgcatgtct    11880
ttagttctat gatgacacaa accccgccca gcgtcttgtc attggcgaat cgaacacgc     11940 agatgcagtc ggggcggcgc ggtccgaggt ccacttcgca tattaaggtg acgcgtgtgg    12000
cctcgaacac cgagcgaccc tgcagcgacc cgcttaacag cgtcaacagc gtgccgcaga    12060
tcccgggggg caatgagata tgaaaaagcc tgaactcacc gcgacgtctg tcgagaagtt    12120
tctgatcgaa aagttcgaca gcgtctccga cctgatgcag ctctcggagg gcgaagaatc    12180
tcgtgctttc agcttcgatg taggagggcg tggatatgtc ctgcgggtaa atagctgcgc    12240
cgatggtttc tacaaagatc gttatgttta tcggcacttt gcatcggccg cgctcccgat    12300
tccggaagtg cttgacattg ggaattcag cgagagcctg acctattgca tctcccgccg     12360
tgcacagggt gtcacgttgc aagacctgcc tgaaaccgaa ctgcccgctg ttctgcagcc    12420
ggtcgcggag gccatggatg cgatcgctgc ggccgatctt agccagacga gcgggttcgg    12480
cccattcgga ccgcaaggaa tcggtcaata cactacatgg cgtgatttca tatgcgcgat    12540
tgctgatccc catgtgtatc actggcaaac tgtgatggac gacaccgtca gtgcgtccgt    12600
cgcgcaggct ctcgatgagc tgatgctttg ggccgaggac tgccccgaag tccggcacct    12660
cgtgcacgcg gatttcggct ccaacaatgt cctgacggac aatggccgca taacagcggt    12720
cattgactgg agcgaggcga tgttcgggga ttcccaatac gaggtcgcca acatcttctt    12780
ctggaggccg tggttggctt gtatggagca gcagacgcgc tacttcgagc ggaggcatcc    12840
ggagcttgca ggatcgccgc ggctccgggc gtatatgctc cgcattggtc ttgaccaact    12900
ctatcagagc ttggttgacg gcaatttcga tgatgcagct tgggcgcagg tcgatgcga    12960 cgcaatcgtc cgatccggag ccgggactgt cgggcgtaca caaatcgccc gcagaagcgc    13020
ggccgtctgg accgatggct gtgtagaagt actcgccgat agtggaaacc gacgcccag    13080 cactcgtccg gatcgggaga tgggggaggc taactgaaac acggaaggag acaataccgg    13140
aaggaacccg cgctatgacg gcaataaaaa gacagaataa aacgcacggg tgttgggtcg    13200
tttgttcata aacgcggggt tcggtcccag ggctggcact ctgtcgatac cccaccgaga    13260
ccccattggg gccaatacgc ccgcgtttct tccttttccc caccccaccc cccaagttcg    13320
ggtgaaggcc cagggctcgc agccaacgtc ggggcggcag gccctgccat agccactggc    13380
cccgtgggtt agggacgggg tccccatgg ggaatggttt atggttcgtg ggggttatta     13440
ttttgggcgt tgcgtggggt caggtccacg actggactga gcagacagac ccatggtttt    13500
tggatggcct gggcatggac cgcatgtact ggcgcgacac gaacaccggg cgtctgtggc    13560
tgccaaacac ccccgacccc caaaaaccac cgcgcggatt tctggcgtgc caagctagtc    13620
gaccaattct catgtttgac agcttatcat cgcagatccg ggcaacgttg ttgccattgc    13680
tgcaggcgca gaactggtag gtatggaaga tctatacatt gaatcaatat tggcaattag    13740
ccatattagt cattggttat atagcataaa tcaatattgg ctattggcca ttgcatacgt    13800
tgtatctata tcataatatg tacatttata ttggctcatg tccaatatga ccgccat      13857
```

<210> SEQ ID NO 7
<211> LENGTH: 13260
<212> TYPE: DNA
<213> ORGANISM: Macaca fascicularis

<400> SEQUENCE: 7

| | | | | | |
|---|---|---|---|---|---|
| gttgacattg | attattgact | agttattaat | agtaatcaat | tacggggtca | ttagttcata | 60 |
| gcccatatat | ggagttccgc | gttacataac | ttacggtaaa | tggcccgcct | ggctgaccgc | 120 |
| ccaacgaccc | ccgcccattg | acgtcaataa | tgacgtatgt | tcccatagta | acgccaatag | 180 |
| ggactttcca | ttgacgtcaa | tgggtggagt | atttacggta | aactgcccac | ttggcagtac | 240 |
| atcaagtgta | tcatatgcca | agtccgcccc | ctattgacgt | caatgacggt | aaatggcccg | 300 |
| cctggcatta | tgcccagtac | atgaccttac | gggactttcc | tacttggcag | tacatctacg | 360 |
| tattagtcat | cgctattacc | atggtgatgc | ggttttggca | gtacaccaat | gggcgtggat | 420 |
| agcggtttga | ctcacgggga | tttccaagtc | tccaccccat | tgacgtcaat | gggagtttgt | 480 |
| tttggcacca | aaatcaacgg | gactttccaa | aatgtcgtaa | taaccccgcc | ccgttgacgc | 540 |
| aaatgggcgt | aggcgtgta | cggtgggagg | tctatataag | cagagctcgt | ttagtgaacc | 600 |
| gtcagatcgc | ctggagacgc | catccacgct | gttttgacct | ccatagaaga | caccgggacc | 660 |
| gatccagcct | ccgcggccgg | gaacggtgca | ttggaacgcg | gattcccgt | gccaagagtg | 720 |
| acgtaagtac | cgcctataga | gtctataggc | ccacctcctt | ggcttcttat | gcatgctata | 780 |
| ctgtttttgg | cttggggtct | atacaccccc | gcttcctcat | gttataggtg | atggtatagc | 840 |
| ttagcctata | ggtgtgggtt | attgaccatt | attgaccact | cccctattgg | tgacgatact | 900 |
| ttccattact | aatccataac | atggctcttt | gccacaactc | tctttattgg | ctatatgcca | 960 |
| atacactgtc | cttcagagac | tgacacggac | tctgtatttt | tacaggatgg | ggtctcattt | 1020 |
| attatttaca | aattcacata | tacaacacca | ccgtccccag | tgcccgcagc | ttttattaaa | 1080 |
| cataacgtgg | gatctccacg | cgaatctcgg | gtacgtgttc | cggacatggg | ctcttctccg | 1140 |
| gtagcggcgg | agcttctaca | tccgagccct | gctcccatgc | ctccagcgac | tcatggtcgc | 1200 |
| tcggcagctc | cttgctccta | acagtggagg | ccagacttag | gcacagcacg | atgcccacca | 1260 |
| ccaccagtgt | gccgcacaag | gccgtggcgg | tagggtatgt | gtctgaaaat | gagctcgggg | 1320 |
| agcgggcttg | caccgctgac | gcatttggaa | gacttaaggc | agcggcagaa | gaagatgcag | 1380 |
| gcagctgagt | tgttgtgttc | tgataagagt | cagaggtaac | tcccgttgcg | gtgctgttaa | 1440 |
| cggtggaggg | cagtgtagtc | tgagcagtac | tcgttgctgc | cgcgcgcgcc | accagacata | 1500 |
| atagctgaca | gactaacaga | ctgttccttt | ccatgggtct | tttctgcagt | caccgtcctt | 1560 |
| agatctgtct | agaagctggg | taccagctgc | tagcaagctt | gccaccatga | gacagacttt | 1620 |
| gccttatacc | tactttggt | ggggactttt | gcccttgggg | atgctgtgtg | catcctccac | 1680 |
| caacaaatgc | actgttagcc | aagaagttgc | tgactgcagc | cacctgaagt | taactcaggt | 1740 |
| acccgatgat | ctccccacaa | acataacagt | gttgaatctt | acccataatc | aactcagaag | 1800 |
| attaccagct | gccaattta | caagatatag | ccaactaact | atcttggatg | taggatttaa | 1860 |
| ctccatctca | aaactggagc | cagaattgtg | ccaaaaactt | cccatgttaa | agttttgaa | 1920 |
| cctccagcac | aatgagctat | ctcaactttc | tgataaaact | tttgccttct | gcacgaattt | 1980 |
| gacggaactc | catctcatgt | ccaactcaat | ccagaaaatt | aaaaataatc | cctttgtaaa | 2040 |
| gcagaagaat | ttaatcacat | tagatctgtc | tcataatggc | ttgtcatcta | caaaattagg | 2100 |
| aactcaggtt | cagctggaaa | atctccaaga | gcttctatta | tcaaacaata | aaatccaagc | 2160 |

```
gctaaaaagt gaagaacttg gtatccttgc caattcatct ttaaaaagt tagagttgtc    2220 atcgaatcaa attaaagagt tttctccagg gtgttttcac gcaattggaa gattattggg    2280 cctcttctg aacaatgtcc agctgggtcc ccgcctcaca gagaagctat gtttggaatt    2340
agcaaacaca agcgttcgga atctgtctct gagtaacagc cagctgtcca ccaccagcaa    2400
tacaactttc ttgggactaa agtggacaaa cctcactatg ctcgatcttt cccacaacaa    2460
cttaaatgtg attggtaacg attcctttgt ttggcttcca catctagaat atttcttcct    2520
ggagtataat aatatacagc atttgctctc tcactctttg cacgggcttt tcaatgtgcg    2580
gtacctgaat ttgaaacggt cttttactaa acaaagtatt tcccttgctt cgctccccaa    2640
gattgatgat ttttcttttc ggtggctaac atgtttggag caccttaaca tggaagataa    2700
tgatatttca ggcataaaaa gcaatatgtt cacaggattg ataaacctga aatacttaag    2760
tctatccaac tccttacaa gtttgcaaac tttgacaaat gaaacatttg tatcacttgc    2820
tcattctccc ttacacatac tcaacctaac caagaataaa atctcaaaaa tagagagtgg    2880
tgccttctct tggttgggcc acctagaagt acttgacttg ggccttaatg aaattgggca    2940
agaactcaca ggccaggaat ggagtggtct agaaaatatt ttcgaaatct atctttccta    3000
caacaagtac ctgcaactga ctaagaactc ctttgccttg gtccgaagcc ttcaacgact    3060
gatgctccga agggtggccc ttaaaaatgt ggattgctct ccttcaccat tccagcctct    3120
tggtaacctg accattctgg atctaagcaa caacaacata gccaacataa atgatgacat    3180
gttggaaggt cttgagaaac tagaaattct ggatttgcag cataacaact tagcacggct    3240
ctggaaacac gcaaaccctg gtggtcctgt ttatttccta aagggtctgt ctcacctcca    3300
catccttaac ttggagtcta atggctttga cgagatccca gttgaggtct tcaaggattt    3360
atctgaacta aagatcattg atttaggatt gaataattta aacacacttc cagcgtctgt    3420
ctttgataat caggtgtctc taaagtcatt gaaccttcag aagaatctca taacatcagt    3480
tgagaagaag gttttcgggc cagctttcag gaacctgagt aacttagata tgcgctttaa    3540
tccctttgat tgcacatgtg aaagtattgc ctggtttgtt aattggatta caagaccca    3600 cgccaacatc cctgagctgt caagccacta cctttgcaac actccacccc actatcatgg    3660
gttcccagtg agacttttg atacatcatc ctgcaaagac agtgccccct ttgaaggatc    3720
ccatcatcac catcaccatt gaagatccag acatgataag atacattgat gagttttggac    3780 aaaccacaac tagaatgcag tgaaaaaat gctttatttg tgaaatttgt gatgctattg    3840
ctttatttgt aaccattata agctgcaata acaagttaa caacaacaat tgcattcatt    3900
ttatgtttca ggtcagggg gaggtgtggg aggttttta aagcaagtaa aacctctaca    3960
aatgtggtat ggctgattat gatccggctg cctcgcgcgt ttcggtgatg acggtgaaaa    4020
cctctgacac atgcagctcc cggagacggt cacagcttgt ctgtaagcgg atgccgggag    4080
cagacaagcc cgtcaggcgt cagcgggtgt tggcgggtgt cggggcgcag ccatgaggtc    4140
gactctagag gatcgatgcc ccgccccgga cgaactaaac ctgactacga catctctgcc    4200
ccttcttcgc ggggcagtgc atgtaatccc ttcagttggt tggtacaact tgccaactgg    4260
gccctgttcc acatgtgaca cgggggggga ccaaacacaa aggggttctc tgactgtagt    4320
tgacatcctt ataatggat gtgcacattt gccaacactg agtggctttc atcctggagc    4380
agactttgca gtctgtggac tgcaacacaa cattgccttt atgtgtaact cttggctgaa    4440
gctcttacac caatgctggg ggacatgtac ctcccagggg cccaggaaga ctacgggagg    4500
ctacaccaac gtcaatcaga ggggcctgtg tagctaccga taagcggacc ctcaagaggg    4560
```

```
cattagcaat agtgtttata aggcccccctt gttaaccccta aacgggtagc atatgcttcc   4620
cgggtagtag tatatactat ccagactaac cctaattcaa tagcatatgt tacccaacgg   4680
gaagcatatg ctatcgaatt agggttagta aaagggtcct aaggaacagc gatatctccc   4740 acccccatgag ctgtcacggt tttatttaca tggggtcagg attccacgag ggtagtgaac   4800
cattttagtc acaagggcag tggctgaaga tcaaggagcg ggcagtgaac tctcctgaat   4860
cttcgcctgc ttcttcattc tccttcgttt agctaataga ataactgctg agttgtgaac   4920
agtaaggtgt atgtgaggtg ctcgaaaaca aggtttcagg tgacgccccc agaataaaat   4980
ttggacgggg ggttcagtgg tggcattgtg ctatgacacc aatataaccc tcacaaaccc   5040
cttgggcaat aaatactagt gtaggaatga aacattctga atatctttaa caatagaaat   5100
ccatggggtg gggacaagcc gtaaagactg gatgtccatc tcacacgaat ttatggctat   5160
gggcaacaca taatcctagt gcaatatgat actggggtta ttaagatgtg tcccaggcag   5220
ggaccaagac aggtgaacca tgttgttaca ctctatttgt aacaagggga aagagagtgg   5280
acgccgacag cagcggactc cactggttgt ctctaacacc cccgaaaatt aaacggggct   5340
ccacgccaat ggggcccata aacaaagaca agtggccact cttttttttg aaattgtgga   5400 gtggggggcac gcgtcagccc ccacacgccg ccctgcggtt ttggactgta aaataagggt   5460
gtaataactt ggctgattgt aaccccgcta accactgcgg tcaaaccact tgcccacaaa   5520
accactaatg gcaccccggg gaatacctgc ataagtaggt gggcgggcca agatagggggc   5580 gcgattgctg cgatctggag gacaaattac acacacttgc gcctgagcgc caagcacagg   5640
gttgttggtc ctcatattca cgaggtcgct gagagcacgg tgggctaatg ttgccatggg   5700
tagcatatac tacccaaata tctggatagc atatgctatc ctaatctata tctgggtagc   5760
ataggctatc ctaatctata tctgggtagc atatgctatc ctaatctata tctgggtagt   5820
atatgctatc ctaatttata tctgggtagc ataggctatc ctaatctata tctgggtagc   5880
atatgctatc ctaatctata tctgggtagt atatgctatc ctaatctgta tccgggtagc   5940
atatgctatc ctaatagaga ttagggtagt atatgctatc ctaatttata tctgggtagc   6000
atatactacc caaatatctg gatagcatat gctatcctaa tctatatctg ggtagcatat   6060
gctatcctaa tctatatctg gtagcatag gctatcctaa tctatatctg ggtagcatat   6120
gctatcctaa tctatatctg ggtagtatat gctatcctaa tttatatctg ggtagcatag   6180
gctatcctaa tctatatctg ggtagcatat gctatcctaa tctatatctg ggtagtatat   6240
gctatcctaa tctgtatccg ggtagcatat gctatcctca tgcatataca gtcagcatat   6300
gatacccagt agtagagtgg gagtgctatc ctttgcatat gccgccacct cccaaggggg   6360 cgtgaattt cgctgcttgt cctttttcctg ctggttgctc ccattcttag gtgaatttaa   6420
ggaggccagg ctaaagccgt cgcatgtctg attgctcacc aggtaaatgt cgctaatgtt   6480
ttccaacgcg agaaggtgtt gagcgcggag ctgagtgacg tgacaacatg ggtatgccca   6540
attgccccat gttgggagga cgaaaatggt gacaagacag atggccagaa atacaccaac   6600
agcacgcatg atgtctactg gggatttatt ctttagtgcg ggggaataca cggctttttaa   6660 tacgattgag ggcgtctcct aacaagttac atcactcctg cccttcctca ccctcatctc   6720
catcacctcc ttcatctccg tcatctccgt catcaccctc cgcggcagcc ccttccacca   6780
taggtggaaa ccagggaggc aaatctactc catcgtcaaa gctgcacaca gtcaccctga   6840
tattgcaggt aggagcgggc tttgtcataa caaggtcctt aatcgcatcc ttcaaaacct   6900
cagcaaatat atgagtttgt aaaaagacca tgaaataaca gacaatggac tcccttagcg   6960
```

```
ggccaggttg tgggccgggt ccaggggcca ttccaaaggg gagacgactc aatggtgtaa    7020
gacgacattg tggaatagca agggcagttc ctcgccttag gttgtaaagg gaggtcttac    7080
tacctccata tacgaacaca ccggcgaccc aagttccttc gtcggtagtc ctttctacgt    7140
gactcctagc caggagagct cttaaacctt ctgcaatgtt ctcaaatttc gggttggaac    7200
ctccttgacc acgatgcttt tccaaaccac cctccttttt tgcgccctgc ctccatcacc    7260
ctgaccccgg ggtccagtgc ttgggccttc tcctgggtca tctgcggggc cctgctctat    7320
cgctcccggg ggcacgtcag gctcaccatc tgggccacct tcttggtggt attcaaaata    7380
atcggcttcc cctacagggt ggaaaaatgg ccttctacct ggagggggcc tgcgcggtgg    7440
agacccggat gatgatgact gactactggg actcctgggc ctcttttctc cacgtccacg    7500
acctctcccc ctggctcttt cacgacttcc cccctggcc ctttcacgtc ctctaccccg    7560
gcggcctcca ctacctcctc gaccccggcc tccactacct cctcgacccc ggcctccact    7620
gcctcctcga ccccggcctc cacctcctgc tcctgcccct cctgctcctg ccctcctcc    7680 tgctcctgcc cctcctgccc ctcctgctcc tgcccctcct gcccctcctg ctcctgcccc    7740
tcctgcccct cctgctcctg cccctcctgc cctcctcct gctcctgccc ctcctgcccc    7800
tcctcctgct cctgcccctc ctgcccctcc tgctcctgcc cctcctgccc ctcctgctcc    7860
tgcccctcct gcccctcctg ctcctgcccc tcctgctcct gcccctcctg ctcctgcccc    7920
tcctgctcct gcccctcctg ctcctgcccc ctcctcct gctcctgccc ctcctgctcc    7980
tgcccctcct gcccctcctg cccctcctgc tcctgcccct cctgctc ctgcccctcc    8040 tgcccctcct gcccctcctc ctgctcctgc cctcctgccc cctcctgccc    8100
tcctcctgct cctgcccctc ctgcccctcc tgcccctcct cctgctcctg cccctcctgc    8160 cctcctcct gtcctgcccc ctcctcctgc tcctgcccct cctgcccct cctgcccctcc    8220 tcctgctcct gcccctcctc ctgctcctgc cctcctgcc cctcctgccc ctcctgcccc    8280
tcctcctgct cctgcccctc ctcctgctcc tgcccctcct gctcctgccc ctcccgctcc    8340
tgctcctgct cctgttccac cgtgggtccc tttgcagcca atgcaacttg gacgttttg    8400 gggtctccgg acaccatctc tatgtcttgg ccctgatcct gagccgcccg gggctcctgg    8460
tcttccgcct cctcgtcctc gtcctcttcc ccgtcctcgt ccatggttat caccccctct    8520
tctttgaggt ccactgccgc cggagccttc tggtccagat gtgtctccct tctctcctag    8580
gccatttcca ggtcctgtac ctggcccctc gtcagacatg attcacacta aaagagatca    8640
atagacatct ttattagacg acgctcagtg aatacaggga gtgcagactc ctgccccctc    8700
caacagcccc cccaccctca tccccttcat ggtcgctgtc agacagatcc aggtctgaaa    8760 attcccatc ctccgaacca tcctcgtcct catcaccaat tactcgcagc ccggaaaact    8820
cccgctgaac atcctcaaga tttgcgtcct gagcctcaag ccaggcctca aattcctcgt    8880 ccccctttt gctggacggt agggatgggg attctcggga cccctcctct tcctcttcaa    8940
ggtcaccaga cagagatgct actgggggcaa cggaagaaaa gctgggtgcg gcctgtgagg    9000
atcagcttat cgatgataag ctgtcaaaca tgagaattct tgaagacgaa agggcctcgt    9060
gatacgccta tttttatagg ttaatgtcat gataataatg gtttcttaga cgtcaggtgg    9120
cacttttcgg ggaaatgtgc gcggaacccc tatttgttta ttttctaaa tacattcaaa    9180 tatgtatccg ctcatgagac aataaccctg ataaatgctt caataatatt gaaaaggaa    9240 gagtatgagt attcaacatt tccgtgtcgc ccttattccc ttttttgcgg cattttgcct    9300
tcctgttttt gctcacccag aaacgctggt gaaagtaaaa gatgctgaag atcagttggg    9360
```

```
tgcacgagtg ggttacatcg aactggatct caacagcggt aagatccttg agagttttcg    9420
ccccgaagaa cgttttccaa tgatgagcac ttttaaagtt ctgctatgtg gcgcggtatt    9480
atcccgtgtt gacgccgggc aagagcaact cggtcgccgc atacactatt ctcagaatga    9540
cttggttgag tactcaccag tcacagaaaa gcatcttacg gatggcatga cagtaagaga    9600
attatgcagt gctgccataa ccatgagtga taacactgcg gccaacttac ttctgacaac    9660
gatcggagga ccgaaggagc taaccgcttt tttgcacaac atgggggatc atgtaactcg    9720
ccttgatcgt tgggaaccgg agctgaatga agccatacca aacgacgagc gtgacaccac    9780
gatgcctgca gcaatggcaa caacgttgcg caaactatta actggcgaac tacttactct    9840
agcttcccgg caacaattaa tagactggat ggaggcggat aaagttgcag gaccacttct    9900
gcgctcggcc cttccggctg gctggtttat tgctgataaa tctggagccg gtgagcgtgg    9960
gtctcgcggt atcattgcag cactggggcc agatggtaag ccctcccgta tcgtagttat   10020
ctacacgacg gggagtcagg caactatgga tgaacgaaat agacagatcg ctgagatagg   10080
tgcctcactg attaagcatt ggtaactgtc agaccaagtt tactcatata ctttagat    10140 tgatttaaaa cttcattttt aatttaaaag gatctaggtg aagatccttt ttgataatat   10200
catgaccaaa atcccttaac gtgagttttc gttccactga gcgtcagacc ccgtagaaaa   10260
gatcaaagga tcttcttgag atcctttttt tctgcgcgta atctgctgct tgcaaacaaa   10320
aaaaccaccg ctaccagcgg tggtttgttt gccggatcaa gagctaccaa ctcttttcc    10380 gaaggtaact ggcttcagca gagcgcagat accaaatact gtccttctag tgtagccgta   10440
gttaggccac cacttcaaga actctgtagc accgcctaca tacctcgctc tgctaatcct   10500
gttaccagtg gctgctgcca gtggcgataa gtcgtgtctt accgggttgg actcaagacg   10560
atagttaccg gataaggcgc agcggtcggg ctgaacgggg ggttcgtgca cacagcccag   10620
cttggagcga acgacctaca ccgaactgag atacctacag cgtgagctat gagaaagcgc   10680
cacgcttccc gaagggagaa aggcggacag gtatccggta agcggcaggg tcggaacagg   10740
agagcgcacg agggagcttc cagggggaaa cgcctggtat ctttatagtc ctgtcgggtt   10800
tcgccacctc tgacttgagc gtcgattttt gtgatgctcg tcaggggggc ggagcctatg   10860
gaaaaacgcc agcaacgcgg cctttttacg gttcctggcc ttttgctggc cttgaagctg   10920
tccctgatgg tcgtcatcta cctgcctgga cagcatggcc tgcaacgcgg gcatcccgat   10980
gccgccggaa gcgagaagaa tcataatggg gaaggccatc cagcctcgcg tcgcgaacgc   11040
cagcaagacg tagcccagcg cgtcggcccc gagatgcgcc gcgtgcggct gctggagatg   11100
gcggacgcga tggatatgtt ctgccaaggg ttggtttgcg cattcacagt tctccgcaag   11160
aattgattgg ctccaattct tggagtggtg aatccgttag cgaggtgccg ccctgcttca   11220
tccccgtggc ccgttgctcg cgtttgctgg cggtgtcccc ggaagaaata tatttgcatg   11280
tctttagttc tatgatgaca caaaccccgc ccagcgtctt gtcattggcg aattcgaaca   11340
cgcagatgca gtcggggcgg cgcggtccga ggtccacttc gcatattaag gtgacgcgtg   11400
tggcctcgaa caccgagcga cccctgcagcg acccgcttaa cagcgtcaac agcgtgccgc   11460
agatcccggg gggcaatgag atatgaaaaa gcctgaactc accgcgacgt ctgtcgagaa   11520
gtttctgatc gaaaagttcg acagcgtctc cgacctgatg cagctctcgg agggcgaaga   11580
atctcgtgct ttcagcttcg atgtaggagg gcgtggatat gtcctgcggg taaatagctg   11640
cgccgatggt ttctacaaag atcgttatgt ttatcggcac tttgcatcgg ccgcgctccc   11700
gattccggaa gtgcttgaca ttggggaatt cagcgagagc ctgacctatt gcatctcccg   11760
```

```
ccgtgcacag ggtgtcacgt tgcaagacct gcctgaaacc gaactgcccg ctgttctgca   11820
gccggtcgcg gaggccatgg atgcgatcgc tgcggccgat cttagccaga cgagcgggtt   11880
cggcccattc ggaccgcaag gaatcggtca atacactaca tggcgtgatt tcatatgcgc   11940
gattgctgat ccccatgtgt atcactggca aactgtgatg gacgacaccg tcagtgcgtc   12000
cgtcgcgcag gctctcgatg agctgatgct tgggccgag gactgccccg aagtccggca   12060
cctcgtgcac gcggatttcg gctccaacaa tgtcctgacg acaatggcc gcataacagc   12120 ggtcattgac tggagcgagg cgatgttcgg ggattcccaa tacgaggtcg ccaacatctt   12180
cttctggagg ccgtggttgg cttgtatgga gcagcagacg cgctacttcg agcggaggca   12240
tccggagctt gcaggatcgc gcggctccg ggcgtatatg ctccgcattg gtcttgacca   12300
actctatcag agcttggttg acggcaattt cgatgatgca gcttgggcgc agggtcgatg   12360
cgacgcaatc gtccgatccg gagccgggac tgtcgggcgt acacaaatcg cccgcagaag   12420
cgcggccgtc tggaccgatg gctgtgtaga agtactcgcc gatagtggaa accgacgccc   12480
cagcactcgt ccggatcggg agatggggga ggctaactga aacacggaag gagacaatac   12540
cggaaggaac ccgcgctatg acggcaataa aagacagaa taaaacgcac gggtgttggg   12600
tcgtttgttc ataaacgcgg ggttcggtcc cagggctggc actctgtcga taccccaccg   12660 agacccatt ggggccaata cgcccgcgtt tcttcctttt ccccacccca ccccccaagt   12720
tcgggtgaag gcccagggct cgcagccaac gtcgggggcgg caggccctgc catagccact   12780
ggccccgtgg gttagggacg gggtccccca tggggaatgg tttatggttc gtggggtta   12840 ttatttgggg cgttgcgtgg ggtcaggtcc acgactggac tgagcagaca gacccatggt   12900
ttttggatgg cctgggcatg gaccgcatgt actggcgcga cacgaacacc gggcgtctgt   12960
ggctgccaaa cacccccgac ccccaaaaac caccgcgcgg atttctggcg tgccaagcta   13020
gtcgaccaat tctcatgttt gacagcttat catcgcagat ccgggcaacg ttgttgccat   13080
tgctgcaggc gcagaactgg taggtatgga agatctatac attgaatcaa tattggcaat   13140
tagccatatt agtcattggt tatatagcat aaatcaatat tggctattgg ccattgcata   13200
cgttgtatct atatcataat atgtacattt atattggctc atgtccaata tgaccgccat   13260
```

<210> SEQ ID NO 8
<211> LENGTH: 681
<212> TYPE: PRT
<213> ORGANISM: Macaca fascicularis

<400> SEQUENCE: 8

```
Ser Thr Asn Lys Cys Thr Val Ser Gln Glu Val Ala Asp Cys Ser His
1               5                   10                  15

Leu Lys Leu Thr Gln Val Pro Asp Asp Leu Pro Thr Asn Ile Thr Val
            20                  25                  30

Leu Asn Leu Thr His Asn Gln Leu Arg Arg Leu Pro Ala Ala Asn Phe
        35                  40                  45

Thr Arg Tyr Ser Gln Leu Thr Ile Leu Asp Val Gly Phe Asn Ser Ile
    50                  55                  60

Ser Lys Leu Glu Pro Glu Leu Cys Gln Lys Leu Pro Met Leu Lys Val
65                  70                  75                  80

Leu Asn Leu Gln His Asn Glu Leu Ser Gln Leu Ser Asp Lys Thr Phe
                85                  90                  95

Ala Phe Cys Thr Asn Leu Thr Glu Leu His Leu Met Ser Asn Ser Ile
            100                 105                 110
```

```
Gln Lys Ile Lys Asn Asn Pro Phe Val Lys Gln Lys Asn Leu Ile Thr
            115                 120                 125
Leu Asp Leu Ser His Asn Gly Leu Ser Ser Thr Lys Leu Gly Thr Gln
    130                 135                 140
Val Gln Leu Glu Asn Leu Gln Glu Leu Leu Ser Asn Asn Lys Ile
145                 150                 155                 160
Gln Ala Leu Lys Ser Glu Glu Leu Gly Ile Leu Ala Asn Ser Ser Leu
                165                 170                 175
Lys Lys Leu Glu Leu Ser Ser Asn Gln Ile Lys Glu Phe Ser Pro Gly
                180                 185                 190
Cys Phe His Ala Ile Gly Arg Leu Leu Gly Leu Phe Leu Asn Asn Val
            195                 200                 205
Gln Leu Gly Pro Arg Leu Thr Glu Lys Leu Cys Leu Glu Leu Ala Asn
    210                 215                 220
Thr Ser Val Arg Asn Leu Ser Leu Ser Asn Ser Gln Leu Ser Thr Thr
225                 230                 235                 240
Ser Asn Thr Thr Phe Leu Gly Leu Lys Trp Thr Asn Leu Thr Met Leu
                245                 250                 255
Asp Leu Ser His Asn Asn Leu Asn Val Ile Gly Asn Asp Ser Phe Val
            260                 265                 270
Trp Leu Pro His Leu Glu Tyr Phe Phe Leu Glu Tyr Asn Asn Ile Gln
    275                 280                 285
His Leu Leu Ser His Ser Leu His Gly Leu Phe Asn Val Arg Tyr Leu
                290                 295                 300
Asn Leu Lys Arg Ser Phe Thr Lys Gln Ser Ile Ser Leu Ala Ser Leu
305                 310                 315                 320
Pro Lys Ile Asp Asp Phe Ser Phe Arg Trp Leu Thr Cys Leu Glu His
            325                 330                 335
Leu Asn Met Glu Asp Asn Asp Ile Ser Gly Ile Lys Ser Asn Met Phe
    340                 345                 350
Thr Gly Leu Ile Asn Leu Lys Tyr Leu Ser Leu Ser Asn Ser Phe Thr
                355                 360                 365
Ser Leu Gln Thr Leu Thr Asn Glu Thr Phe Val Ser Leu Ala His Ser
    370                 375                 380
Pro Leu His Ile Leu Asn Leu Thr Lys Asn Lys Ile Ser Lys Ile Glu
385                 390                 395                 400
Ser Gly Ala Phe Ser Trp Leu Gly His Leu Glu Val Leu Asp Leu Gly
                405                 410                 415
Leu Asn Glu Ile Gly Gln Glu Leu Thr Gly Gln Glu Trp Ser Gly Leu
            420                 425                 430
Glu Asn Ile Phe Glu Ile Tyr Leu Ser Tyr Asn Lys Tyr Leu Gln Leu
    435                 440                 445
Thr Lys Asn Ser Phe Ala Leu Val Arg Ser Leu Gln Arg Leu Met Leu
450                 455                 460
Arg Arg Val Ala Leu Lys Asn Val Asp Cys Ser Pro Ser Pro Phe Gln
465                 470                 475                 480
Pro Leu Gly Asn Leu Thr Ile Leu Asp Leu Ser Asn Asn Asn Ile Ala
                485                 490                 495
Asn Ile Asn Asp Asp Met Leu Glu Gly Leu Glu Lys Leu Glu Ile Leu
            500                 505                 510
Asp Leu Gln His Asn Asn Leu Ala Arg Leu Trp Lys His Ala Asn Pro
    515                 520                 525
Gly Gly Pro Val Tyr Phe Leu Lys Gly Leu Ser His Leu His Ile Leu
530                 535                 540
```

```
Asn Leu Glu Ser Asn Gly Phe Asp Glu Ile Pro Val Glu Val Phe Lys
545                 550                 555                 560

Asp Leu Ser Glu Leu Lys Ile Ile Asp Leu Gly Leu Asn Asn Leu Asn
                565                 570                 575

Thr Leu Pro Ala Ser Val Phe Asp Asn Gln Val Ser Leu Lys Ser Leu
            580                 585                 590

Asn Leu Gln Lys Asn Leu Ile Thr Ser Val Glu Lys Lys Val Phe Gly
                595                 600                 605

Pro Ala Phe Arg Asn Leu Ser Asn Leu Asp Met Arg Phe Asn Pro Phe
            610                 615                 620

Asp Cys Thr Cys Glu Ser Ile Ala Trp Phe Val Asn Trp Ile Asn Lys
625                 630                 635                 640

Thr His Ala Asn Ile Pro Glu Leu Ser Ser His Tyr Leu Cys Asn Thr
                645                 650                 655

Pro Pro His Tyr His Gly Phe Pro Val Arg Leu Phe Asp Thr Ser Ser
            660                 665                 670

Cys Lys Asp Ser Ala Pro Phe Glu Leu
            675                 680

<210> SEQ ID NO 9
<211> LENGTH: 703
<212> TYPE: PRT
<213> ORGANISM: Macaca fascicularis

<400> SEQUENCE: 9

Arg Gln Thr Leu Pro Tyr Thr Tyr Phe Trp Trp Gly Leu Leu Pro Phe
1               5                   10                  15

Gly Met Leu Cys Ala Ser Ser Thr Asn Lys Cys Thr Val Ser Gln Glu
            20                  25                  30

Val Ala Asp Cys Ser His Leu Lys Leu Thr Gln Val Pro Asp Asp Leu
        35                  40                  45

Pro Thr Asn Ile Thr Val Leu Asn Leu Thr His Asn Gln Leu Arg Arg
    50                  55                  60

Leu Pro Ala Ala Asn Phe Thr Arg Tyr Ser Gln Leu Thr Ile Leu Asp
65                  70                  75                  80

Val Gly Phe Asn Ser Ile Ser Lys Leu Glu Pro Glu Leu Cys Gln Lys
                85                  90                  95

Leu Pro Met Leu Lys Val Leu Asn Leu Gln His Asn Glu Leu Ser Gln
            100                 105                 110

Leu Ser Asp Lys Thr Phe Ala Phe Cys Thr Asn Leu Thr Glu Leu His
        115                 120                 125

Leu Met Ser Asn Ser Ile Gln Lys Ile Lys Asn Asn Pro Phe Val Lys
    130                 135                 140

Gln Lys Asn Leu Ile Thr Leu Asp Leu Ser His Asn Gly Leu Ser Ser
145                 150                 155                 160

Thr Lys Leu Gly Thr Gln Val Gln Leu Glu Asn Leu Gln Glu Leu Leu
                165                 170                 175

Leu Ser Asn Asn Lys Ile Gln Ala Leu Lys Ser Glu Glu Leu Gly Ile
            180                 185                 190

Leu Ala Asn Ser Ser Leu Lys Lys Leu Glu Leu Ser Ser Asn Gln Ile
        195                 200                 205

Lys Glu Phe Ser Pro Gly Cys Phe His Ala Ile Gly Arg Leu Leu Gly
    210                 215                 220

Leu Phe Leu Asn Asn Val Gln Leu Gly Pro Arg Leu Thr Glu Lys Leu
225                 230                 235                 240
```

```
Cys Leu Glu Leu Ala Asn Thr Ser Val Arg Asn Leu Ser Leu Ser Asn
                245                 250                 255

Ser Gln Leu Ser Thr Thr Ser Asn Thr Thr Phe Leu Gly Leu Lys Trp
            260                 265                 270

Thr Asn Leu Thr Met Leu Asp Leu Ser His Asn Asn Leu Asn Val Ile
                275                 280                 285

Gly Asn Asp Ser Phe Val Trp Leu Pro His Leu Glu Tyr Phe Phe Leu
        290                 295                 300

Glu Tyr Asn Asn Ile Gln His Leu Leu Ser His Ser Leu His Gly Leu
305                 310                 315                 320

Phe Asn Val Arg Tyr Leu Asn Leu Lys Arg Ser Phe Thr Lys Gln Ser
                325                 330                 335

Ile Ser Leu Ala Ser Leu Pro Lys Ile Asp Asp Phe Ser Phe Arg Trp
                340                 345                 350

Leu Thr Cys Leu Glu His Leu Asn Met Glu Asp Asn Asp Ile Ser Gly
            355                 360                 365

Ile Lys Ser Asn Met Phe Thr Gly Leu Ile Asn Leu Lys Tyr Leu Ser
        370                 375                 380

Leu Ser Asn Ser Phe Thr Ser Leu Gln Thr Leu Thr Asn Glu Thr Phe
385                 390                 395                 400

Val Ser Leu Ala His Ser Pro Leu His Ile Leu Asn Leu Thr Lys Asn
                405                 410                 415

Lys Ile Ser Lys Ile Glu Ser Gly Ala Phe Ser Trp Leu Gly His Leu
                420                 425                 430

Glu Val Leu Asp Leu Gly Leu Asn Glu Ile Gly Gln Glu Leu Thr Gly
            435                 440                 445

Gln Glu Trp Ser Gly Leu Glu Asn Ile Phe Glu Ile Tyr Leu Ser Tyr
        450                 455                 460

Asn Lys Tyr Leu Gln Leu Thr Lys Asn Ser Phe Ala Leu Val Arg Ser
465                 470                 475                 480

Leu Gln Arg Leu Met Leu Arg Arg Val Ala Leu Lys Asn Val Asp Cys
                485                 490                 495

Ser Pro Ser Pro Phe Gln Pro Leu Gly Asn Leu Thr Ile Leu Asp Leu
                500                 505                 510

Ser Asn Asn Asn Ile Ala Asn Ile Asn Asp Asp Met Leu Glu Gly Leu
            515                 520                 525

Glu Lys Leu Glu Ile Leu Asp Leu Gln His Asn Asn Leu Ala Arg Leu
        530                 535                 540

Trp Lys His Ala Asn Pro Gly Gly Pro Val Tyr Phe Leu Lys Gly Leu
545                 550                 555                 560

Ser His Leu His Ile Leu Asn Leu Glu Ser Asn Gly Phe Asp Glu Ile
                565                 570                 575

Pro Val Glu Val Phe Lys Asp Leu Ser Glu Leu Lys Ile Ile Asp Leu
            580                 585                 590

Gly Leu Asn Asn Leu Asn Thr Leu Pro Ala Ser Val Phe Asp Asn Gln
        595                 600                 605

Val Ser Leu Lys Ser Leu Asn Leu Gln Lys Asn Leu Ile Thr Ser Val
            610                 615                 620

Glu Lys Lys Val Phe Gly Pro Ala Phe Arg Asn Leu Ser Asn Leu Asp
625                 630                 635                 640

Met Arg Phe Asn Pro Phe Asp Cys Thr Cys Glu Ser Ile Ala Trp Phe
                645                 650                 655

Val Asn Trp Ile Asn Lys Thr His Ala Asn Ile Pro Glu Leu Ser Ser
```

```
                   660                 665                 670
His Tyr Leu Cys Asn Thr Pro Pro His Tyr His Gly Phe Pro Val Arg
            675                 680                 685

Leu Phe Asp Thr Ser Ser Cys Lys Asp Ser Ala Pro Phe Glu Leu
            690                 695                 700

<210> SEQ ID NO 10
<211> LENGTH: 881
<212> TYPE: PRT
<213> ORGANISM: Macaca fascicularis

<400> SEQUENCE: 10

Ser Thr Asn Lys Cys Thr Val Ser Gln Glu Val Ala Asp Cys Ser His
1               5                   10                  15

Leu Lys Leu Thr Gln Val Pro Asp Asp Leu Pro Thr Asn Ile Thr Val
            20                  25                  30

Leu Asn Leu Thr His Asn Gln Leu Arg Arg Leu Pro Ala Ala Asn Phe
        35                  40                  45

Thr Arg Tyr Ser Gln Leu Thr Ile Leu Asp Val Gly Phe Asn Ser Ile
    50                  55                  60

Ser Lys Leu Glu Pro Glu Leu Cys Gln Lys Leu Pro Met Leu Lys Val
65                  70                  75                  80

Leu Asn Leu Gln His Asn Glu Leu Ser Gln Leu Ser Asp Lys Thr Phe
                85                  90                  95

Ala Phe Cys Thr Asn Leu Thr Glu Leu His Leu Met Ser Asn Ser Ile
            100                 105                 110

Gln Lys Ile Lys Asn Asn Pro Phe Val Lys Gln Lys Asn Leu Ile Thr
        115                 120                 125

Leu Asp Leu Ser His Asn Gly Leu Ser Ser Thr Lys Leu Gly Thr Gln
    130                 135                 140

Val Gln Leu Glu Asn Leu Gln Glu Leu Leu Leu Ser Asn Asn Lys Ile
145                 150                 155                 160

Gln Ala Leu Lys Ser Glu Glu Leu Gly Ile Leu Ala Asn Ser Ser Leu
                165                 170                 175

Lys Lys Leu Glu Leu Ser Ser Asn Gln Ile Lys Glu Phe Ser Pro Gly
            180                 185                 190

Cys Phe His Ala Ile Gly Arg Leu Leu Gly Leu Phe Leu Asn Asn Val
        195                 200                 205

Gln Leu Gly Pro Arg Leu Thr Glu Lys Leu Cys Leu Glu Leu Ala Asn
    210                 215                 220

Thr Ser Val Arg Asn Leu Ser Leu Ser Asn Ser Gln Leu Ser Thr Thr
225                 230                 235                 240

Ser Asn Thr Thr Phe Leu Gly Leu Lys Trp Thr Asn Leu Thr Met Leu
                245                 250                 255

Asp Leu Ser His Asn Asn Leu Asn Val Ile Gly Asn Asp Ser Phe Val
            260                 265                 270

Trp Leu Pro His Leu Glu Tyr Phe Phe Leu Glu Tyr Asn Asn Ile Gln
        275                 280                 285

His Leu Leu Ser His Ser Leu His Gly Leu Phe Asn Val Arg Tyr Leu
    290                 295                 300

Asn Leu Lys Arg Ser Phe Thr Lys Gln Ser Ile Ser Leu Ala Ser Leu
305                 310                 315                 320

Pro Lys Ile Asp Asp Phe Ser Phe Arg Trp Leu Thr Cys Leu Glu His
                325                 330                 335

Leu Asn Met Glu Asp Asn Asp Ile Ser Gly Ile Lys Ser Asn Met Phe
```

```
                340             345             350
Thr Gly Leu Ile Asn Leu Lys Tyr Leu Ser Leu Ser Asn Ser Phe Thr
            355             360             365
Ser Leu Gln Thr Leu Thr Asn Glu Thr Phe Val Ser Leu Ala His Ser
            370             375             380
Pro Leu His Ile Leu Asn Leu Thr Lys Asn Lys Ile Ser Lys Ile Glu
385             390             395             400
Ser Gly Ala Phe Ser Trp Leu Gly His Leu Glu Val Leu Asp Leu Gly
                405             410             415
Leu Asn Glu Ile Gly Gln Glu Leu Thr Gly Gln Glu Trp Ser Gly Leu
            420             425             430
Glu Asn Ile Phe Glu Ile Tyr Leu Ser Tyr Asn Lys Tyr Leu Gln Leu
            435             440             445
Thr Lys Asn Ser Phe Ala Leu Val Arg Ser Leu Gln Arg Leu Met Leu
            450             455             460
Arg Arg Val Ala Leu Lys Asn Val Asp Cys Ser Pro Ser Pro Phe Gln
465             470             475             480
Pro Leu Gly Asn Leu Thr Ile Leu Asp Leu Ser Asn Asn Asn Ile Ala
                485             490             495
Asn Ile Asn Asp Asp Met Leu Glu Gly Leu Glu Lys Leu Glu Ile Leu
            500             505             510
Asp Leu Gln His Asn Asn Leu Ala Arg Leu Trp Lys His Ala Asn Pro
            515             520             525
Gly Gly Pro Val Tyr Phe Leu Lys Gly Leu Ser His Leu His Ile Leu
            530             535             540
Asn Leu Glu Ser Asn Gly Phe Asp Glu Ile Pro Val Glu Val Phe Lys
545             550             555             560
Asp Leu Ser Glu Leu Lys Ile Ile Asp Leu Gly Leu Asn Asn Leu Asn
                565             570             575
Thr Leu Pro Ala Ser Val Phe Asp Asn Gln Val Ser Leu Lys Ser Leu
            580             585             590
Asn Leu Gln Lys Asn Leu Ile Thr Ser Val Glu Lys Lys Val Phe Gly
            595             600             605
Pro Ala Phe Arg Asn Leu Ser Asn Leu Asp Met Arg Phe Asn Pro Phe
            610             615             620
Asp Cys Thr Cys Glu Ser Ile Ala Trp Phe Val Asn Trp Ile Asn Lys
625             630             635             640
Thr His Ala Asn Ile Pro Glu Leu Ser Ser His Tyr Leu Cys Asn Thr
                645             650             655
Pro Pro His Tyr His Gly Phe Pro Val Arg Leu Phe Asp Thr Ser Ser
            660             665             670
Cys Lys Asp Ser Ala Pro Phe Glu Leu Phe Phe Met Ile Asn Thr Ser
            675             680             685
Ile Leu Leu Ile Phe Ile Phe Val Val Leu Leu Ile His Phe Glu Gly
            690             695             700
Trp Arg Ile Ser Phe Tyr Trp Asn Val Ser Val His Arg Val Leu Gly
705             710             715             720
Phe Lys Glu Ile Asp Arg Gln Thr Glu Gln Phe Glu Tyr Ala Ala Tyr
                725             730             735
Ile Ile His Ala His Lys Asp Lys Asp Trp Val Trp Glu His Phe Ser
            740             745             750
Ser Met Glu Lys Glu Asp Gln Ser Leu Lys Phe Cys Leu Glu Glu Arg
            755             760             765
```

```
Asp Phe Glu Ala Gly Val Phe Glu Leu Glu Ala Ile Val Asn Ser Ile
        770                 775                 780

Lys Arg Ser Arg Lys Ile Ile Phe Ile Ile Thr His His Leu Leu Lys
785                 790                 795                 800

Asp Pro Leu Cys Lys Arg Phe Lys Val His His Ala Val Gln Gln Ala
                805                 810                 815

Ile Glu Gln Asn Leu Asp Ser Ile Ile Leu Phe Leu Glu Glu Ile
        820                 825                 830

Pro Asp Tyr Lys Leu Asn His Ala Leu Cys Leu Arg Arg Gly Met Phe
            835                 840                 845

Lys Ser His Cys Ile Leu Asn Trp Pro Val Gln Lys Glu Arg Ile Gly
850                 855                 860

Ala Phe His His Lys Leu Gln Val Ala Leu Gly Ser Lys Asn Ser Val
865                 870                 875                 880

His

<210> SEQ ID NO 11
<211> LENGTH: 903
<212> TYPE: PRT
<213> ORGANISM: Macaca fascicularis

<400> SEQUENCE: 11

Arg Gln Thr Leu Pro Tyr Thr Tyr Phe Trp Trp Gly Leu Leu Pro Phe
1               5                   10                  15

Gly Met Leu Cys Ala Ser Ser Thr Asn Lys Cys Thr Val Ser Gln Glu
            20                  25                  30

Val Ala Asp Cys Ser His Leu Lys Leu Thr Gln Val Pro Asp Asp Leu
        35                  40                  45

Pro Thr Asn Ile Thr Val Leu Asn Leu Thr His Asn Gln Leu Arg Arg
    50                  55                  60

Leu Pro Ala Ala Asn Phe Thr Arg Tyr Ser Gln Leu Thr Ile Leu Asp
65                  70                  75                  80

Val Gly Phe Asn Ser Ile Ser Lys Leu Glu Pro Glu Leu Cys Gln Lys
                85                  90                  95

Leu Pro Met Leu Lys Val Leu Asn Leu Gln His Asn Glu Leu Ser Gln
            100                 105                 110

Leu Ser Asp Lys Thr Phe Ala Phe Cys Thr Asn Leu Thr Glu Leu His
        115                 120                 125

Leu Met Ser Asn Ser Ile Gln Lys Ile Lys Asn Asn Pro Phe Val Lys
    130                 135                 140

Gln Lys Asn Leu Ile Thr Leu Asp Leu Ser His Asn Gly Leu Ser Ser
145                 150                 155                 160

Thr Lys Leu Gly Thr Gln Val Gln Leu Glu Asn Leu Gln Glu Leu Leu
                165                 170                 175

Leu Ser Asn Asn Lys Ile Gln Ala Leu Lys Ser Glu Glu Leu Gly Ile
            180                 185                 190

Leu Ala Asn Ser Ser Leu Lys Lys Leu Glu Leu Ser Ser Asn Gln Ile
        195                 200                 205

Lys Glu Phe Ser Pro Gly Cys Phe His Ala Ile Gly Arg Leu Leu Gly
    210                 215                 220

Leu Phe Leu Asn Asn Val Gln Leu Gly Pro Arg Leu Thr Glu Lys Leu
225                 230                 235                 240

Cys Leu Glu Leu Ala Asn Thr Ser Val Arg Asn Leu Ser Leu Ser Asn
                245                 250                 255

Ser Gln Leu Ser Thr Thr Ser Asn Thr Thr Phe Leu Gly Leu Lys Trp
```

-continued

```
                260                 265                 270
Thr Asn Leu Thr Met Leu Asp Leu Ser His Asn Asn Leu Asn Val Ile
                275                 280                 285
Gly Asn Asp Ser Phe Val Trp Leu Pro His Leu Glu Tyr Phe Phe Leu
            290                 295                 300
Glu Tyr Asn Asn Ile Gln His Leu Leu Ser His Ser Leu His Gly Leu
305                 310                 315                 320
Phe Asn Val Arg Tyr Leu Asn Leu Lys Arg Ser Phe Thr Lys Gln Ser
                325                 330                 335
Ile Ser Leu Ala Ser Leu Pro Lys Ile Asp Asp Phe Ser Phe Arg Trp
            340                 345                 350
Leu Thr Cys Leu Glu His Leu Asn Met Glu Asp Asn Asp Ile Ser Gly
                355                 360                 365
Ile Lys Ser Asn Met Phe Thr Gly Leu Ile Asn Leu Lys Tyr Leu Ser
        370                 375                 380
Leu Ser Asn Ser Phe Thr Ser Leu Gln Thr Leu Thr Asn Glu Thr Phe
385                 390                 395                 400
Val Ser Leu Ala His Ser Pro Leu His Ile Leu Asn Leu Thr Lys Asn
                405                 410                 415
Lys Ile Ser Lys Ile Glu Ser Gly Ala Phe Ser Trp Leu Gly His Leu
            420                 425                 430
Glu Val Leu Asp Leu Gly Leu Asn Glu Ile Gly Gln Glu Leu Thr Gly
                435                 440                 445
Gln Glu Trp Ser Gly Leu Glu Asn Ile Phe Glu Ile Tyr Leu Ser Tyr
            450                 455                 460
Asn Lys Tyr Leu Gln Leu Thr Lys Asn Ser Phe Ala Leu Val Arg Ser
465                 470                 475                 480
Leu Gln Arg Leu Met Leu Arg Arg Val Ala Leu Lys Asn Val Asp Cys
                485                 490                 495
Ser Pro Ser Pro Phe Gln Pro Leu Gly Asn Leu Thr Ile Leu Asp Leu
            500                 505                 510
Ser Asn Asn Asn Ile Ala Asn Ile Asn Asp Asp Met Leu Glu Gly Leu
        515                 520                 525
Glu Lys Leu Glu Ile Leu Asp Leu Gln His Asn Asn Leu Ala Arg Leu
        530                 535                 540
Trp Lys His Ala Asn Pro Gly Gly Pro Val Tyr Phe Leu Lys Gly Leu
545                 550                 555                 560
Ser His Leu His Ile Leu Asn Leu Glu Ser Asn Gly Phe Asp Glu Ile
                565                 570                 575
Pro Val Glu Val Phe Lys Asp Leu Ser Glu Leu Lys Ile Ile Asp Leu
            580                 585                 590
Gly Leu Asn Asn Leu Asn Thr Leu Pro Ala Ser Val Phe Asp Asn Gln
        595                 600                 605
Val Ser Leu Lys Ser Leu Asn Leu Gln Lys Asn Leu Ile Thr Ser Val
            610                 615                 620
Glu Lys Lys Val Phe Gly Pro Ala Phe Arg Asn Leu Ser Asn Leu Asp
625                 630                 635                 640
Met Arg Phe Asn Pro Phe Asp Cys Thr Cys Glu Ser Ile Ala Trp Phe
                645                 650                 655
Val Asn Trp Ile Asn Lys Thr His Ala Asn Ile Pro Glu Leu Ser Ser
            660                 665                 670
His Tyr Leu Cys Asn Thr Pro Pro His Tyr His Gly Phe Pro Val Arg
        675                 680                 685
```

| Leu | Phe | Asp | Thr | Ser | Ser | Cys | Lys | Asp | Ser | Ala | Pro | Phe | Glu | Leu | Phe |
| | 690 | | | | 695 | | | | 700 | | | | | | |

| Phe | Met | Ile | Asn | Thr | Ser | Ile | Leu | Leu | Ile | Phe | Ile | Phe | Val | Val | Leu |
| 705 | | | | | 710 | | | | | 715 | | | | | 720 |

| Leu | Ile | His | Phe | Glu | Gly | Trp | Arg | Ile | Ser | Tyr | Trp | Asn | Val | Ser |
| | | | | 725 | | | | | 730 | | | | | 735 |

| Val | His | Arg | Val | Leu | Gly | Phe | Lys | Glu | Ile | Asp | Arg | Gln | Thr | Glu | Gln |
| | | | 740 | | | | | 745 | | | | | 750 | | |

| Phe | Glu | Tyr | Ala | Ala | Tyr | Ile | Ile | His | Ala | His | Lys | Asp | Lys | Asp | Trp |
| | | | 755 | | | | | 760 | | | | | 765 | | |

| Val | Trp | Glu | His | Phe | Ser | Met | Glu | Lys | Glu | Asp | Gln | Ser | Leu | Lys |
| | 770 | | | | | 775 | | | | | 780 | | | |

| Phe | Cys | Leu | Glu | Glu | Arg | Asp | Phe | Glu | Ala | Gly | Val | Phe | Glu | Leu | Glu |
| 785 | | | | | 790 | | | | | 795 | | | | | 800 |

| Ala | Ile | Val | Asn | Ser | Ile | Lys | Arg | Ser | Arg | Lys | Ile | Ile | Phe | Ile | Ile |
| | | | | 805 | | | | | 810 | | | | | 815 | |

| Thr | His | His | Leu | Leu | Lys | Asp | Pro | Leu | Cys | Lys | Arg | Phe | Lys | Val | His |
| | | | | 820 | | | | | 825 | | | | | 830 | |

| His | Ala | Val | Gln | Gln | Ala | Ile | Glu | Gln | Asn | Leu | Asp | Ser | Ile | Ile | Leu |
| | | | 835 | | | | | 840 | | | | | 845 | | |

| Ile | Phe | Leu | Glu | Glu | Ile | Pro | Asp | Tyr | Lys | Leu | Asn | His | Ala | Leu | Cys |
| 850 | | | | | 855 | | | | | 860 | | | | | |

| Leu | Arg | Arg | Gly | Met | Phe | Lys | Ser | His | Cys | Ile | Leu | Asn | Trp | Pro | Val |
| 865 | | | | | 870 | | | | | 875 | | | | | 880 |

| Gln | Lys | Glu | Arg | Ile | Gly | Ala | Phe | His | His | Lys | Leu | Gly | Val | Ala | Leu |
| | | | | 885 | | | | | 890 | | | | | 895 | |

| Gly | Ser | Lys | Asn | Ser | Val | His |
| | | | | 900 | | |

<210> SEQ ID NO 12
<211> LENGTH: 2712
<212> TYPE: DNA
<213> ORGANISM: Homo sapiens

<400> SEQUENCE: 12

```
atgagacaga ctttgccttg tatctacttt tggggggggcc ttttgccctt tgggatgctg      60
tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca gaagattacc agccgccaac ttcacaaggt atagccagct aactagcttg     240
gatgtaggat ttaacaccat ctcaaaactg gagccagaat gtgccagaa acttcccatg       300
ttaaagtttt tgaacctcca gcacaatgag ctatctcaac tttctgataa aacctttgcc     360
ttctgcacga atttgactga actccatctc atgtccaact caatccagaa aattaaaaat     420
aatccctttg tcaagcagaa gaatttaatc acattagatc tgtctcataa tggcttgtca     480
tctacaaaat taggaactca ggttcagctg gaaaatctcc aagagcttct attatcaaac     540
aataaaattc aagcgctaaa aagtgaagaa ctggatatct ttgccaattc atctttaaaa     600
aaattagagt tgtcatcgaa tcaaattaaa gagttttctc agggtgtttt tcacgcaatt     660
ggaagattat ttgccctctt tctgaacaat gtccagctgg gtccagcct acagagaag       720
ctatgtttgg aattagcaaa cacaagcatt cggaatctgt ctctgagtaa cagccagctg    780
tccaccacca gcaatacaac tttcttggga ctaaagtgga caaatctcac tatgctcgat    840
cttttcctaca caacttaaa tgtggttggt aacgattcct tgcttggct tccacaacta     900
```

```
gaatatttct tcctagagta taataatata cagcatttgt tttctcactc tttgcacggg    960
cttttcaatg tgaggtacct gaatttgaaa cggtcttta ctaaacaaag tatttccctt    1020
gcctcactcc ccaagattga tgatttttct tttcagtggc taaaatgttt ggagcacctt   1080
aacatggaag ataatgatat tccaggcata aaaagcaata tgttcacagg attgataaac   1140
ctgaaatact taagtctatc caactccttt acaagtttgc gaactttgac aaatgaaaca   1200
tttgtatcac ttgctcattc tcccttacac atactcaacc taaccaagaa taaaatctca   1260
aaaatagaga gtgatgcttt ctcttggttg ggccacctag aagtacttga cctgggcctt   1320
aatgaaattg ggcaagaact cacaggccag gaatggagag gtctagaaaa tattttcgaa   1380
atctatcttt cctacaacaa gtacctgcag ctgactagga actcctttgc cttggtccca   1440
agccttcaac gactgatgct ccgaaggggtg gcccttaaaa atgtggatag ctctccttca   1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct tgacgagat cccagttgag   1740
gtcttcaagg atttatttga actaaagatc atcgatttag gattgaataa tttaaacaca   1800
cttccagcat ctgtctttaa taatcaggtg tctctaaagt cattgaacct tcagaagaat   1860
ctcataacat ccgttgagaa gaaggtttc gggccagctt tcaggaaacct gactgagtta   1920
gatatgcgct ttaatccctt tgattgcacg tgtgaaagta ttgcctggtt tgttaattgg   1980
attaacgaga cccataccaa catccctgag ctgtcaagcc actacctttg caacactcca   2040
cctcactatc atgggttccc agtgagactt tttgatacat catcttgcaa agacagtgcc   2100
ccctttgaac tctttttcat gatcaatacc agtatcctgt tgatttttat ctttattgta   2160
cttctcatcc actttgaggg ctggaggata tcttttttatt ggaatgtttc agtacatcga   2220
gttcttggtt tcaaagaaat agacagacag acagaacagt tgaatatgc agcatatata   2280
attcatgcct ataaagataa ggattgggtc tgggaacatt tctcttcaat ggaaaaggaa   2340
gaccaatctc tcaaattttg tctggaagaa agggactttg aggcgggtgt ttttgaacta   2400
gaagcaattg ttaacagcat caaaagaagc agaaaaatta ttttgttat aacacaccat   2460
ctattaaaag acccattatg caaaagattc aaggtacatc atgcagttca acaagctatt   2520
gaacaaaatc tggattccat tatattggtt ttcctgagg agattccaga ttataaactg   2580
aaccatgcac tctgtttgcg aagaggaatg tttaaatctc actgcatctt gaactggcca   2640
gttcagaaag aacggatagg tgcctttcgt cataaattgc aagtagcact tggatccaaa   2700
aactctgtac at                                                       2712
```

<210> SEQ ID NO 13
<211> LENGTH: 904
<212> TYPE: PRT
<213> ORGANISM: Homo sapiens

<400> SEQUENCE: 13

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg

```
                50                   55                   60
Arg Leu Pro Ala Ala Asn Phe Thr Arg Tyr Ser Gln Leu Thr Ser Leu
65                   70                   75                   80

Asp Val Gly Phe Asn Thr Ile Ser Lys Leu Glu Pro Glu Leu Cys Gln
                    85                   90                   95

Lys Leu Pro Met Leu Lys Val Leu Asn Leu Gln His Asn Glu Leu Ser
                   100                  105                  110

Gln Leu Ser Asp Lys Thr Phe Ala Phe Cys Thr Asn Leu Thr Glu Leu
                   115                  120                  125

His Leu Met Ser Asn Ser Ile Gln Lys Ile Lys Asn Asn Pro Phe Val
130                  135                  140

Lys Gln Lys Asn Leu Ile Thr Leu Asp Leu Ser His Asn Gly Leu Ser
145                  150                  155                  160

Ser Thr Lys Leu Gly Thr Gln Val Gln Leu Glu Asn Leu Gln Glu Leu
                   165                  170                  175

Leu Leu Ser Asn Asn Lys Ile Gln Ala Leu Lys Ser Glu Glu Leu Asp
                   180                  185                  190

Ile Phe Ala Asn Ser Ser Leu Lys Lys Leu Glu Leu Ser Ser Asn Gln
                   195                  200                  205

Ile Lys Glu Phe Ser Pro Gly Cys Phe His Ala Ile Gly Arg Leu Phe
210                  215                  220

Gly Leu Phe Leu Asn Asn Val Gln Leu Gly Pro Ser Leu Thr Glu Lys
225                  230                  235                  240

Leu Cys Leu Glu Leu Ala Asn Thr Ser Ile Arg Asn Leu Ser Leu Ser
                   245                  250                  255

Asn Ser Gln Leu Ser Thr Thr Ser Asn Thr Thr Phe Leu Gly Leu Lys
                   260                  265                  270

Trp Thr Asn Leu Thr Met Leu Asp Leu Ser Tyr Asn Asn Leu Asn Val
          275                  280                  285

Val Gly Asn Asp Ser Phe Ala Trp Leu Pro Gln Leu Glu Tyr Phe Phe
290                  295                  300

Leu Glu Tyr Asn Asn Ile Gln His Leu Phe Ser His Ser Leu His Gly
305                  310                  315                  320

Leu Phe Asn Val Arg Tyr Leu Asn Leu Lys Arg Ser Phe Thr Lys Gln
                   325                  330                  335

Ser Ile Ser Leu Ala Ser Leu Pro Lys Ile Asp Asp Phe Ser Phe Gln
                   340                  345                  350

Trp Leu Lys Cys Leu Glu His Leu Asn Met Glu Asp Asn Asp Ile Pro
          355                  360                  365

Gly Ile Lys Ser Asn Met Phe Thr Gly Leu Ile Asn Leu Lys Tyr Leu
370                  375                  380

Ser Leu Ser Asn Ser Phe Thr Ser Leu Arg Thr Leu Thr Asn Glu Thr
385                  390                  395                  400

Phe Val Ser Leu Ala His Ser Pro Leu His Ile Leu Asn Leu Thr Lys
                   405                  410                  415

Asn Lys Ile Ser Lys Ile Glu Ser Asp Ala Phe Ser Trp Leu Gly His
                   420                  425                  430

Leu Glu Val Leu Asp Leu Gly Leu Asn Glu Ile Gly Gln Glu Leu Thr
                   435                  440                  445

Gly Gln Glu Trp Arg Gly Leu Glu Asn Ile Phe Glu Ile Tyr Leu Ser
          450                  455                  460

Tyr Asn Lys Tyr Leu Gln Leu Thr Arg Asn Ser Phe Ala Leu Val Pro
465                  470                  475                  480
```

-continued

```
Ser Leu Gln Arg Leu Met Leu Arg Arg Val Ala Leu Lys Asn Val Asp
            485                 490                 495

Ser Ser Pro Ser Pro Phe Gln Pro Leu Arg Asn Leu Thr Ile Leu Asp
        500                 505                 510

Leu Ser Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
        530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
                580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
        610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
        690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
        770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
        850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900
```

<210> SEQ ID NO 14
<211> LENGTH: 42
<212> TYPE: DNA
<213> ORGANISM: Artificial Sequence
<220> FEATURE:
<223> OTHER INFORMATION: Chemically synthesized polynucleotide primer
    for PCR amplification of polynucleotides encoding
    cynoTLR3 peptide chains.

<400> SEQUENCE: 14
cccaagcttg ccaccatgag acagactttg ccttgtatct ac                             42

<210> SEQ ID NO 15
<211> LENGTH: 40
<212> TYPE: DNA
<213> ORGANISM: Artificial Sequence
<220> FEATURE:
<223> OTHER INFORMATION: Chemically synthesized polynucleotide primer
    for PCR amplification of polynucleotides encoding
    cynoTLR3 peptide chains.

<400> SEQUENCE: 15
cccctcgagt taatgtacag agtttttgga tccaagtgct                                40

<210> SEQ ID NO 16
<211> LENGTH: 32
<212> TYPE: DNA
<213> ORGANISM: Artificial Sequence
<220> FEATURE:
<223> OTHER INFORMATION: Chemically synthesized polynucleotide primer
    for PCR amplification of polynucleotides encoding
    cynoTLR3 peptide chains.

<400> SEQUENCE: 16
catggatcct tcaaaggggg cactgtcttt gc                                        32

<210> SEQ ID NO 17
<211> LENGTH: 29
<212> TYPE: DNA
<213> ORGANISM: Artificial Sequence
<220> FEATURE:
<223> OTHER INFORMATION: Chemically synthesized polynucleotide primer
    for PCR amplification of polynucleotides encoding
    cynoTLR3 peptide chains.

<400> SEQUENCE: 17
cactgttatg tttgtgggga gatcatcgg                                            29

<210> SEQ ID NO 18
<211> LENGTH: 30
<212> TYPE: DNA
<213> ORGANISM: Artificial Sequence
<220> FEATURE:
<223> OTHER INFORMATION: Chemically synthesized polynucleotide primer
    for PCR amplification of polynucleotides encoding
    cynoTLR3 peptide chains.

<400> SEQUENCE: 18
atcctacatc caagatagtt agttggctat                                           30

<210> SEQ ID NO 19
<211> LENGTH: 23
<212> TYPE: DNA
<213> ORGANISM: Artificial Sequence
<220> FEATURE:
<223> OTHER INFORMATION: Chemically synthesized polynucleotide primer
    for PCR amplification of polynucleotides encoding
    cynoTLR3 peptide chains.

<400> SEQUENCE: 19
caaggtacat catgccgttc aac   23

<210> SEQ ID NO 20
<211> LENGTH: 904
<212> TYPE: PRT
<213> ORGANISM: Macaca fascicularis

<400> SEQUENCE: 20

```
Met Arg Gln Thr Leu Pro Tyr Thr Tyr Phe Trp Trp Gly Leu Leu Pro
1               5                   10                  15

Phe Gly Met Leu Cys Ala Ser Ser Thr Asn Lys Cys Thr Val Ser Gln
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ile Leu
65                  70                  75                  80

Asp Val Gly Phe Asn Ser Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Gly
            180                 185                 190

Ile Leu Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Leu
    210                 215                 220

Gly Leu Phe Leu Asn Asn Val Gln Leu Gly Pro Arg Leu Thr Glu Lys
225                 230                 235                 240

Leu Cys Leu Glu Leu Ala Asn Thr Ser Val Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser His Asn Asn Leu Asn Val
        275                 280                 285

Ile Gly Asn Asp Ser Phe Val Trp Leu Pro His Leu Glu Tyr Phe Phe
    290                 295                 300

Leu Glu Tyr Asn Asn Ile Gln His Leu Leu Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Arg
            340                 345                 350

Trp Leu Thr Cys Leu Glu His Leu Asn Met Glu Asp Asn Asp Ile Ser
```

```
            355                 360                 365
Gly Ile Lys Ser Asn Met Phe Thr Gly Leu Ile Asn Leu Lys Tyr Leu
    370                 375                 380

Ser Leu Ser Asn Ser Phe Thr Ser Leu Gln Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Gly Ala Phe Ser Trp Leu Gly His
                420                 425                 430

Leu Glu Val Leu Asp Leu Gly Leu Asn Glu Ile Gly Gln Glu Leu Thr
                435                 440                 445

Gly Gln Glu Trp Ser Gly Leu Glu Asn Ile Phe Glu Ile Tyr Leu Ser
    450                 455                 460

Tyr Asn Lys Tyr Leu Gln Leu Thr Lys Asn Ser Phe Ala Leu Val Arg
465                 470                 475                 480

Ser Leu Gln Arg Leu Met Leu Arg Arg Val Ala Leu Lys Asn Val Asp
                485                 490                 495

Cys Ser Pro Ser Pro Phe Gln Pro Leu Gly Asn Leu Thr Ile Leu Asp
                500                 505                 510

Leu Ser Asn Asn Asn Ile Ala Asn Ile Asn Asp Asp Met Leu Glu Gly
                515                 520                 525

Leu Glu Lys Leu Glu Ile Leu Asp Leu Gln His Asn Asn Leu Ala Arg
    530                 535                 540

Leu Trp Lys His Ala Asn Pro Gly Gly Pro Val Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Ser Glu Leu Lys Ile Ile Asp
                580                 585                 590

Leu Gly Leu Asn Asn Leu Asn Thr Leu Pro Ala Ser Val Phe Asp Asn
    595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Ser Asn Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Lys Thr His Ala Asn Ile Pro Glu Leu Ser
                660                 665                 670

Ser His Tyr Leu Cys Asn Thr Pro Pro His Tyr His Gly Phe Pro Val
                675                 680                 685

Arg Leu Phe Asp Thr Ser Ser Cys Lys Asp Ser Ala Pro Phe Glu Leu
    690                 695                 700

Phe Phe Met Ile Asn Thr Ser Ile Leu Leu Ile Phe Ile Phe Val Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
                740                 745                 750

Gln Phe Glu Tyr Ala Ala Tyr Ile Ile His Ala His Lys Asp Lys Asp
    755                 760                 765

Trp Val Trp Glu His Phe Ser Ser Met Glu Lys Glu Asp Gln Ser Leu
    770                 775                 780
```

```
Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Ile
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Ile Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe His His Lys Leu Gln Val Ala
                885                 890                 895

Leu Gly Ser Lys Asn Ser Val His
            900

<210> SEQ ID NO 21
<211> LENGTH: 2715
<212> TYPE: DNA
<213> ORGANISM: Macaca fascicularis

<400> SEQUENCE: 21
atgagacaga ctttgcctta tacctacttt tggtggggac ttttgcccct tgggatgctg      60
tgtgcatcct ccaccaacaa atgcactgtt agccaagaag ttgctgactg cagccacctg     120
aagttaactc aggtacccga tgatctcccc acaaacataa cagtgttgaa tcttacccat     180
aatcaactca gaagattacc agctgccaat tttacaagat atagccaact aactatcttg     240
gatgtaggat taactccat ctcaaaactg gagccagaat tgtgccaaaa acttcccatg      300
ttaaagtttt tgaacctcca gcacaatgag ctatctcaac tttctgataa aacttttgcc     360
ttctgcacga atttgacgga actccatctc atgtccaact caatccagaa aattaaaaat     420
aatccctttg taaagcagaa gaatttaatc acattagatc tgtctcataa tggcttgtca     480
tctacaaaat taggaactca ggttcagctg aaaatctccc aagagcttct attatcaaac     540
aataaaatcc aagcgctaaa aagtgaagaa cttggtatcc ttgccaattc atcttttaaa     600
aagttagagt tgtcatcgaa tcaaattaaa gagttttctc agggtgtttt tcacgcaatt     660
ggaagattat tgggcctctt tctgaacaat gtccagctgg gtccccgcct cacagagaag     720
ctatgtttgg aattagcaaa cacaagcgtt cggaatctgt ctctgagtaa cagccagctg     780
tccaccacca gcaatacaac tttcttggga ctaaagtgga caaacctcac tatgctcgat     840 cttttcccaca caacttaaa tgtgattggt aacgattcct tgtttggct tccacatcta     900 gaatatttct tcctggagta taataatata cagcatttgc tctctcactc tttgcacggg     960
cttttcaatg tgcggtacct gaatttgaaa cggtcttta ctaaacaaag tatttccctt     1020
gcttcgctcc ccaagattga tgatttttct tttcggtggc taacatgttt ggagcacctt     1080
aacatggaag ataatgatat ttcaggcata aaaagcaata tgttcacagg attgataaac     1140
ctgaaatact taagtctatc caactccttt acaagtttgc aaactttgac aaatgaaaca     1200
tttgtatcac ttgctcattc tcccttacac atactcaacc taaccaagaa taaaatctca     1260
aaaatagaga gtggtgcctt ctcttggttg ggccacctag aagtacttga cttgggcctt     1320
aatgaaattg ggcaagaact cacaggccag gaatggagtg gtctagaaaa atttttcgaa     1380
atctatcttt cctacaacaa gtacctgcaa ctgactaaga actccttgc cttggtccga     1440
```

| | |
|---|---|
| agccttcaac gactgatgct ccgaaggtg gcccttaaaa atgtggattg ctctccttca | 1500 |
| ccattccagc ctcttggtaa cctgaccatt ctggatctaa gcaacaacaa catagccaac | 1560 |
| ataaatgatg acatgttgga aggtcttgag aaactagaaa ttctggattt gcagcataac | 1620 |
| aacttagcac ggctctggaa acacgcaaac cctggtggtc ctgtttattt cctaaagggt | 1680 |
| ctgtctcacc tccacatcct taacttggag tctaatggct ttgacgagat cccagttgag | 1740 |
| gtcttcaagg atttatctga actaaagatc attgatttag gattgaataa tttaaacaca | 1800 |
| cttccagcgt ctgtctttga taatcaggtg tctctaaagt cattgaacct tcagaagaat | 1860 |
| ctcataacat cagttgagaa gaaggttttc gggccagctt tcaggaacct gagtaactta | 1920 |
| gatatgcgct ttaatccctt tgattgcaca tgtgaaagta ttgcctggtt tgttaattgg | 1980 |
| attaacaaga cccacgccaa catccctgag ctgtcaagcc actacctttg caacactcca | 2040 |
| ccccactatc atgggttccc agtgagactt tttgatacat catcctgcaa agacagtgcc | 2100 |
| ccctttgaac tcttttcat gatcaatacc agtatcctgt tgatttttat ctttgttgta | 2160 |
| cttctcatcc actttgaggg ctggaggata tcttttact ggaatgtttc agtacatcga | 2220 |
| gttcttggtt tcaaagaaat agacagacag acagaacagt ttgaatatgc agcatatata | 2280 |
| attcacgccc ataaagataa ggattgggtc tgggaacatt tctcttcaat ggaaaaggaa | 2340 |
| gaccaatctc tcaaattttg tctggaagaa agggactttg aggcaggtgt ttttgaactg | 2400 |
| gaagcaattg ttaacagcat caaaagaagc agaaaaatta tttttattat aacacaccat | 2460 |
| ctattaaaag acccattatg caaaagattc aaggtacatc atgccgttca acaagctatt | 2520 |
| gaacaaaatc tggattccat tatattgatt ttccttgagg agattccaga ttataaactg | 2580 |
| aaccatgcac tctgttttgcg aagaggaatg tttaaatctc actgcatctt gaactggcca | 2640 |
| gttcagaaag aacggatagg tgcctttcat cataaactgc aagtagcact tggatccaaa | 2700 |
| aactcagtac attaa | 2715 |

<210> SEQ ID NO 22
<211> LENGTH: 2712
<212> TYPE: DNA
<213> ORGANISM: Macaca mulatta

<400> SEQUENCE: 22

| | |
|---|---|
| atgagacaga ctttgcctta tacctacttt tggtggggac ttttgcccct tgggatgctg | 60 |
| tgtgcatcct ccaccaacaa atgcactgtt agccaagaag ttgctgactg cagccacctg | 120 |
| aagttaactc aggtacccga tgatctcccc acaaacataa cagtgttgaa tcttacccat | 180 |
| aatcaactca gaagattacc agctgccaat tttacaagat atagccaact aactatcttg | 240 |
| gatgtaggat ttaactccat ctcaaaaccg gagccagaat tgtgccaaaa acttcccatg | 300 |
| ttaaaagttt tgaacctcca gcacaatgag ctatctcaac tttccgataa aacttttgcc | 360 |
| ttctgcatga atttgacgga actccattcc ctgtcccact caatccagaa aattaaaaat | 420 |
| aatccctttg tcaagcagaa gaatttaatc acattagatc tgtctcataa tggcttgtca | 480 |
| tctataaaat taggaactca ggttcagatg gaaaatctcc aagagcttct attatcaaac | 540 |
| aataaaatcc aagcgctaaa aagtgaagaa cttggtatcc ttgccaattc atcttaaaaa | 600 |
| aagttagagt tgtcatcgaa tcaaattaaa gagttttctc cagggtgttt tcacgcaatt | 660 |
| ggaagatcat tgggcctctt cctgaacaat gtccagctgg gtccccgcct cacagagaag | 720 |
| ctatgtttgg aattagcaaa cacaagcgtt cggaatctgt ctctgagtaa cagccagctg | 780 |
| tctaccacca gcaatacaac tttcttggga ctaaagtgga caaacctcac tatgcttgat | 840 |

```
ctttcccaca acaacttaaa tgtggttggt aacgattcct ttgcttggct tccacaacta    900
gaatatttct tcctggagta taataatata cagcatttgc tctctcactc tttgcacggg    960
cttttcaatg tgcggtacct gaatttgaaa cggtctttta ctaaacaaag tatttccctt   1020
gcttcgctcc ccaagattga tgattttctc tttcggtggc taacatgttt ggagcacctt   1080
aacatggaag ataatgatat tcaggcata aaaagcaata tgttcacagg attgataaac    1140
ctgaaatact taagtctatc caactccttt acaagtttgc aaactttgac aaatgaaaca   1200
tttgtatcac ttgctcattc tcccttacac atactcaacc taaccaagaa taaaatctca   1260
aaaatagaga gtggtgcctt tcttggttg ggccacctag aagtacttga cttgggcctt    1320
aatgaaattg ggcaagaact cacaggccag gaatggagtg gtctagaaaa tattttcgaa   1380
atctatcttt cctacaacaa gtacctgcaa ctgactaaga actccttgc cttggtccga    1440
agccttcaac gactgatgct ccgaaggtg gcccttaaaa atgtggattg ctctccttca    1500
ccattccagc tcttggtaa cctgaccatt ctggatctaa gcaacaacaa catagccaac    1560
ataaatgatg acatgttgga aggtcttgag aaactagaaa ttctggattt gcagcataac   1620
aacttagcac ggctctggaa acacgcaaac cctggtggtc ctgtttattt cctaaagggt   1680
ctgtctcacc tccacatcct taacttggag tctaatggct ttgacgagat cccagttgag   1740
gtcttcaagg atttatctga actaaagatc attgatttag gattgaataa tttaaacaca   1800
cttccagcgt ctgtctttga taatcaggtg tctctaaagt cattgaacct tcagaagaat   1860
ctcataacat cagttgagaa gaaggttttc gggccagctt tcaggaacct gagtaactta   1920
gatatgcgct ttaatcccct tgattgcaca tgtgaaagta ttgcctggtt tgttaattgg   1980
attagcaaga cccacgccaa catccctgag ctgtcaagcc actaccttg caacactcca    2040
ccccactatc atgggttccc agtgagactt tttgatacat catcctgcaa agacagtgcc   2100
ccctttgaac tctttttcat tatcaatacc agtatcctgt tgatttgtat ctttgttgta   2160
cttctcatcc actttgaggg ctggaggata tctttttact ggaatgtttc agtacatcga   2220
gttcttggtt tcaaagaaat agacagacag acagaacagt ttgaatatgc agcatatata   2280
attcacgccc ataaagataa ggattgggtc tgggaacatt tctcttcaat ggaaaaggaa   2340
gaccaatctc tcaaattttg tctggaagaa agggactttg aggcaggtgt ttttgaactg   2400
gaagcaattg ttaacagcat caaaagaagc agaaaaatta ttttattat aacacaccat   2460
ctattaaaag acccattatg caaaagattc aaggtacatc atgccgttca acaagctatt   2520
gaacaaaatc tggattccat tatattgatt tccttgagg agattccaga ttataaactg    2580
aaccatgcac tctgtttgcg aagaggaatg tttaaatctc actgcatctt gaactggcca   2640
gttcagaaag aacggatagg tgcctttcat cataaactgc aagtagcact tggatccaaa   2700
aactcagtac at                                                      2712

<210> SEQ ID NO 23
<211> LENGTH: 904
<212> TYPE: PRT
<213> ORGANISM: Macaca mulatta

<400> SEQUENCE: 23

Met Arg Gln Thr Leu Pro Tyr Thr Tyr Phe Trp Trp Gly Leu Leu Pro
 1               5                  10                  15

Phe Gly Met Leu Cys Ala Ser Ser Thr Asn Lys Cys Thr Val Ser Gln
            20                  25                  30

Glu Val Ala Asp Cys Ser His Leu Lys Leu Thr Gln Val Pro Asp Asp
        35                  40                  45
```

```
Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ile Leu
65                  70                  75                  80

Asp Val Gly Phe Asn Ser Ile Ser Lys Pro Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Met Asn Leu Thr Glu Leu
        115                 120                 125

His Ser Leu Ser His Ser Ile Gln Lys Ile Lys Asn Asn Pro Phe Val
130                 135                 140

Lys Gln Lys Asn Leu Ile Thr Leu Asp Leu Ser His Asn Gly Leu Ser
145                 150                 155                 160

Ser Ile Lys Leu Gly Thr Gln Val Gln Met Glu Asn Leu Gln Glu Leu
                165                 170                 175

Leu Leu Ser Asn Asn Lys Ile Gln Ala Leu Lys Ser Glu Glu Leu Gly
                180                 185                 190

Ile Leu Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Ser Leu
210                 215                 220

Gly Leu Phe Leu Asn Asn Val Gln Leu Gly Pro Arg Leu Thr Glu Lys
225                 230                 235                 240

Leu Cys Leu Glu Leu Ala Asn Thr Ser Val Arg Asn Leu Ser Leu Ser
                245                 250                 255

Asn Ser Gln Leu Ser Thr Thr Ser Asn Thr Thr Phe Leu Gly Leu Lys
                260                 265                 270

Trp Thr Asn Leu Thr Met Leu Asp Leu Ser His Asn Asn Leu Asn Val
        275                 280                 285

Val Gly Asn Asp Ser Phe Ala Trp Leu Pro Gln Leu Glu Tyr Phe Phe
290                 295                 300

Leu Glu Tyr Asn Asn Ile Gln His Leu Leu Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Arg
                340                 345                 350

Trp Leu Thr Cys Leu Glu His Leu Asn Met Glu Asp Asn Asp Ile Ser
        355                 360                 365

Gly Ile Lys Ser Asn Met Phe Thr Gly Leu Ile Asn Leu Lys Tyr Leu
370                 375                 380

Ser Leu Ser Asn Ser Phe Thr Ser Leu Gln Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Gly Ala Phe Ser Trp Leu Gly His
                420                 425                 430

Leu Glu Val Leu Asp Leu Gly Leu Asn Glu Ile Gly Gln Glu Leu Thr
        435                 440                 445
```

Gly Gln Glu Trp Ser Gly Leu Glu Asn Ile Phe Glu Ile Tyr Leu Ser
450                 455                 460

Tyr Asn Lys Tyr Leu Gln Leu Thr Lys Asn Ser Phe Ala Leu Val Arg
465                 470                 475                 480

Ser Leu Gln Arg Leu Met Leu Arg Arg Val Ala Leu Lys Asn Val Asp
                485                 490                 495

Cys Ser Pro Ser Pro Phe Gln Pro Leu Gly Asn Leu Thr Ile Leu Asp
            500                 505                 510

Leu Ser Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
530                 535                 540

Leu Trp Lys His Ala Asn Pro Gly Gly Pro Val Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Ser Glu Leu Lys Ile Ile Asp
            580                 585                 590

Leu Gly Leu Asn Asn Leu Asn Thr Leu Pro Ala Ser Val Phe Asp Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Ser Asn Leu
625                 630                 635                 640

Asp Met Arg Phe Asn Pro Phe Asp Cys Thr Cys Glu Ser Ile Ala Trp
                645                 650                 655

Phe Val Asn Trp Ile Ser Lys Thr His Ala Asn Ile Pro Glu Leu Ser
            660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
    690                 695                 700

Phe Phe Ile Ile Asn Thr Ser Ile Leu Leu Ile Cys Ile Phe Val Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala His Lys Asp Lys Asp
        755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Ile
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Ile Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

```
Val Gln Lys Glu Arg Ile Gly Ala Phe His His Lys Leu Gln Val Ala
                885                 890                 895

Leu Gly Ser Lys Asn Ser Val His
            900
```